(12) United States Patent
Maltz

(10) Patent No.: US 11,311,747 B2
(45) Date of Patent: Apr. 26, 2022

(54) SYSTEMS AND METHODS FOR ISOCENTER CALIBRATION

(71) Applicant: UIH AMERICA, INC., Houston, TX (US)

(72) Inventor: Jonathan Maltz, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 0 days.

(21) Appl. No.: 16/931,393

(22) Filed: Jul. 16, 2020

(65) Prior Publication Data

US 2020/0346042 A1 Nov. 5, 2020

(51) Int. Cl.
*A61N 5/10* (2006.01)
*G06T 11/00* (2006.01)
(Continued)

(52) U.S. Cl.
CPC .......... *A61N 5/1075* (2013.01); *A61B 6/035* (2013.01); *A61B 6/037* (2013.01); *A61B 6/0407* (2013.01);
(Continued)

(58) Field of Classification Search
CPC .......... A61N 5/1075; A61N 2005/1076; G06T 11/005; G06T 7/0012; G06T 7/60;
(Continued)

(56) References Cited

U.S. PATENT DOCUMENTS

| | | | | |
|---|---|---|---|---|
| 2013/0267829 A1* | 10/2013 | Ojha | .................... | A61B 6/4417 600/411 |
| 2015/0085993 A1* | 3/2015 | Scheib | ................ | A61N 5/1049 378/207 |

(Continued)

FOREIGN PATENT DOCUMENTS

| | | |
|---|---|---|
| CN | 103632364 A | 3/2014 |
| CN | 104933718 A | 9/2015 |

(Continued)

OTHER PUBLICATIONS

Du, Weiliang et al., A Quality Assurance Procedure to Evaluate Cone-Beam CT Image Center Congruence with the Radiation Isocenter of a Linear Accelerator, Journal of Applied Clinical Medical Physics, 11(4): 15-26, 2010.
First Office Action in Chinese Application No. 201910256465.6 dated Jul. 3, 2020, 16 pages.

*Primary Examiner* — David P Porta
*Assistant Examiner* — Mamadou Faye
(74) *Attorney, Agent, or Firm* — Metis IP LLC

(57) ABSTRACT

The present disclosure is related to systems and methods for isocenter calibration. The method includes providing a phantom including a first member and a second member with a fixed position relationship. The method includes acquiring, using a first device, at least one first image of the first member of the phantom. The method includes determining, based on the at least one first image, a first position relationship between a first isocenter of the first device and the first member. The method includes acquiring, using a second device, at least one second image of the second member of the phantom. The method includes determining, based on the at least one second image and the fixed position relationship, a second position relationship between a second isocenter of the second device and the first member. The method includes determining, based on the first position relationship and the second position relationship, a third position relationship between the first isocenter and the second isocenter.

20 Claims, 9 Drawing Sheets

(51) Int. Cl.
*G06T 7/00* (2017.01)
*G06T 7/60* (2017.01)
*A61B 6/00* (2006.01)
*A61B 6/03* (2006.01)
*A61B 6/04* (2006.01)

(52) U.S. Cl.
CPC ............ *A61B 6/584* (2013.01); *G06T 7/0012* (2013.01); *G06T 7/60* (2013.01); *G06T 11/005* (2013.01); *A61N 2005/1076* (2013.01); *G06T 2207/30096* (2013.01)

(58) Field of Classification Search
CPC .......... G06T 2207/30096; A61B 6/584; A61B 6/035; A61B 6/037; A61B 6/0407; A61B 6/583; A61B 6/582; A61B 6/032
See application file for complete search history.

(56) References Cited

U.S. PATENT DOCUMENTS

2017/0027540 A1   2/2017   Sjölund
2018/0300901 A1   10/2018  Wakai et al.
2019/0175951 A1*  6/2019   Yu ........................ A61B 6/4064

FOREIGN PATENT DOCUMENTS

| CN | 105371759 A | 3/2016 |
| CN | 105469418 A | 4/2016 |
| CN | 106097300 A | 11/2016 |
| CN | 106780624 A | 5/2017 |
| CN | 109242915 A | 1/2019 |
| CN | 109908497 A | 6/2019 |
| JP | H10122819 A | 5/1998 |
| JP | 2017116280 A | 6/2017 |

* cited by examiner

SYSTEMS AND METHODS FOR ISOCENTER CALIBRATION

TECHNICAL FIELD

The present disclosure generally relates to systems and methods for radiation therapy, and more particularly, to systems and methods for isocenter calibration in radiation therapy.

BACKGROUND

Radiation therapy (RT) is widely used in clinical treatment for cancers and other conditions of a patient. Kilovoltage (kV) X-ray images (e.g., computed tomography (CT) images) are used in RT to guide a patient setup prior to an RT treatment delivery. Compared to megavoltage (MV) portal images, kV X-ray images generally offer better visualization of bony anatomy, thus making it easier to align the patient to a planned position. Conventionally, a CT image may be acquired using an imaging device (e.g., a CT device) which is spaced by a distance from a treatment device. The patient may need to be moved to different positions for imaging and treatment. In such cases, in order to deliver an accuracy RT treatment to the patient based on the CT image, it may be beneficial to determine a geometrical relationship between an isocenter of the treatment device (e.g., an isocenter of MV treatment beams) and an isocenter of the imaging device (e.g., an isocenter indicated on a CT image). Thus, it is desirable to develop systems and methods for isocenter calibration in radiation therapy.

SUMMARY

According to an aspect of the present disclosure, a method for isocenter calibration may be implemented on a computing device having one or more processors and one or more storage devices. The method may include providing a phantom including a first member and a second member with a fixed position relationship. The method may include acquiring, using a first device, at least one first image of the first member of the phantom. The method may include determining, based on the at least one first image, a first position relationship between a first isocenter of the first device and the first member. The method may include acquiring, using a second device, at least one second image of the second member of the phantom. The method may include determining, based on the at least one second image and the fixed position relationship between the first member and the second member, a second position relationship between a second isocenter of the second device and the first member. The method may include determining, based on the first position relationship and the second position relationship, a third position relationship between the first isocenter of the first device and the second isocenter of the second device.

In some embodiments, the method may include determining a radiation field center in each of the at least one first image. The method may include determining position information of the first member in the each of the at least one first image. The method may include determining the first position relationship based on the radiation field center and the position information of the first member in the each of the at least one first image.

In some embodiments, the method may include determining position information of the second member in each of the at least one second image. The method may include determining position information of the first member in the each of the at least one second image based on the position information of the second member in the each of the at least one second image and the fixed position relationship between the first member and the second member. The method may include determining the second position relationship based on the position information of the first member in the each of the at least one second image.

In some embodiments, the method may include placing the phantom at a first position with respect to the first device before the acquisition of the at least one first image. The method may include causing a couch to move the phantom from the first position to a second position with respect to the second device after the acquisition of the at least one first image and before the acquisition of the at least one second image.

In some embodiments, the method may include determining one or more translation and rotation components of the couch during the movement of the couch.

In some embodiments, the method may include determining whether the third position relationship satisfies a preset condition. The method may include adjusting one of the first device or the second device in response to determining that the third position relationship does not satisfy the preset condition.

In some embodiments, the first device may include a megavoltage (MV) treatment source. The second device may include a kilovoltage (kV) imaging source.

In some embodiments, a first radius of the first member may be larger than a second radius of the second member.

In some embodiments, the first member may be made of a first material, the second member may be made of a second material. An atomic number of the first material may be higher than an atomic number of the second material.

In some embodiments, the first material may include a metal, and the second material may include plastic.

In some embodiments, the first member and the second member may be connected by a coupling member.

In some embodiments, the coupling member may have a first end corresponding to the first member and a second end corresponding to the second member. At least one end of the first end or the second end of the coupling member may extend beyond a corresponding member of the phantom.

In some embodiments, the phantom may include a second coupling member disposed at an angle with the coupling member.

In some embodiments, the first device may include a positron emission tomography (PET) device or a single photon emission computed tomography (SPECT) device, and the second device may include a CT device.

In some embodiments, a PET and/or SPECT imageable isotope may be present in the phantom.

According to an aspect of the present disclosure, a method for isocenter calibration may be implemented on a computing device having one or more processors and one or more storage devices. The method may include providing a phantom including a first member and a second member with a fixed position relationship. The method may include acquiring, using a first device, a plurality of first images of the first member of the phantom. The method may include determining, based on the plurality of first images, a position of a first isocenter of the first device. The method may include acquiring, using a second device, a plurality of second images of the second member of the phantom. The method may include determining, based on the plurality of second images and the fixed position relationship between the first member and the second member, a position of a second isocenter of the second device. The method may include determining, based on the position of the first isocenter and the position of the second isocenter, a position relationship between the first isocenter of the first device and the second isocenter of the second device.

In some embodiments, the method may include determining position information of the first member in each of the plurality of first images. The method may include determining the position of the first isocenter based on the position information of the first member in the each of the plurality of first images.

In some embodiments, the method may include determining position information of the second member in each of the plurality of second images. The method may include determining position information of the first member in the each of the plurality of second images based on the position information of the second member in the each of the plurality of second images and the fixed position relationship between the first member and the second member. The method may include determining the position of the second isocenter based on the position information of the first member in the each of the plurality of second images.

In some embodiments, the method may include determining a first isocenter distribution based on the plurality of first images. The method may include determining a second isocenter distribution based on the plurality of second images.

According to another aspect of the present disclosure, a system for isocenter calibration may include at least one storage device storing a set of instructions, and at least one processor in communication with the at least one storage device. When executing the stored set of instructions, the at least one processor may cause the system to perform a method. The method may include providing a phantom including a first member and a second member with a fixed position relationship. The method may include acquiring, using a first device, at least one first image of the first member of the phantom. The method may include determining, based on the at least one first image, a first position relationship between a first isocenter of the first device and the first member. The method may include acquiring, using a second device, at least one second image of the second member of the phantom. The method may include determining, based on the at least one second image and the fixed position relationship between the first member and the second member, a second position relationship between a second isocenter of the second device and the first member. The method may include determining, based on the first position relationship and the second position relationship, a third position relationship between the first isocenter of the first device and the second isocenter of the second device.

According to another aspect of the present disclosure, a system for isocenter calibration may include at least one storage device storing a set of instructions, and at least one processor in communication with the at least one storage device. When executing the stored set of instructions, the at least one processor may cause the system to perform a method. The method may include providing a phantom including a first member and a second member with a fixed position relationship. The method may include acquiring, using a first device, a plurality of first images of the first member of the phantom. The method may include determining, based on the plurality of first images, a position of a first isocenter of the first device. The method may include acquiring, using a second device, a plurality of second images of the second member of the phantom. The method may include determining, based on the plurality of second images and the fixed position relationship between the first member and the second member, a position of a second isocenter of the second device. The method may include determining, based on the position of the first isocenter and the position of the second isocenter, a position relationship between the first isocenter of the first device and the second isocenter of the second device.

According to still another aspect of the present disclosure, a non-transitory computer readable medium may include at least one set of instructions. When executed by at least one processor of a computing device, the at least one set of instructions may cause the at least one processor to effectuate a method. The method may include providing a phantom including a first member and a second member with a fixed position relationship. The method may include acquiring, using a first device, at least one first image of the first member of the phantom. The method may include determining, based on the at least one first image, a first position relationship between a first isocenter of the first device and the first member. The method may include acquiring, using a second device, at least one second image of the second member of the phantom. The method may include determining, based on the at least one second image and the fixed position relationship between the first member and the second member, a second position relationship between a second isocenter of the second device and the first member. The method may include determining, based on the first position relationship and the second position relationship, a third position relationship between the first isocenter of the first device and the second isocenter of the second device.

According to still another aspect of the present disclosure, a non-transitory computer readable medium may include at least one set of instructions. When executed by at least one processor of a computing device, the at least one set of instructions may cause the at least one processor to effectuate a method. The method may include providing a phantom including a first member and a second member with a fixed position relationship. The method may include acquiring, using a first device, a plurality of first images of the first member of the phantom. The method may include determining, based on the plurality of first images, a position of a first isocenter of the first device. The method may include acquiring, using a second device, a plurality of second images of the second member of the phantom. The method may include determining, based on the plurality of second images and the fixed position relationship between the first member and the second member, a position of a second isocenter of the second device. The method may include determining, based on the position of the first isocenter and the position of the second isocenter, a position relationship between the first isocenter of the first device and the second isocenter of the second device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are nonlimiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
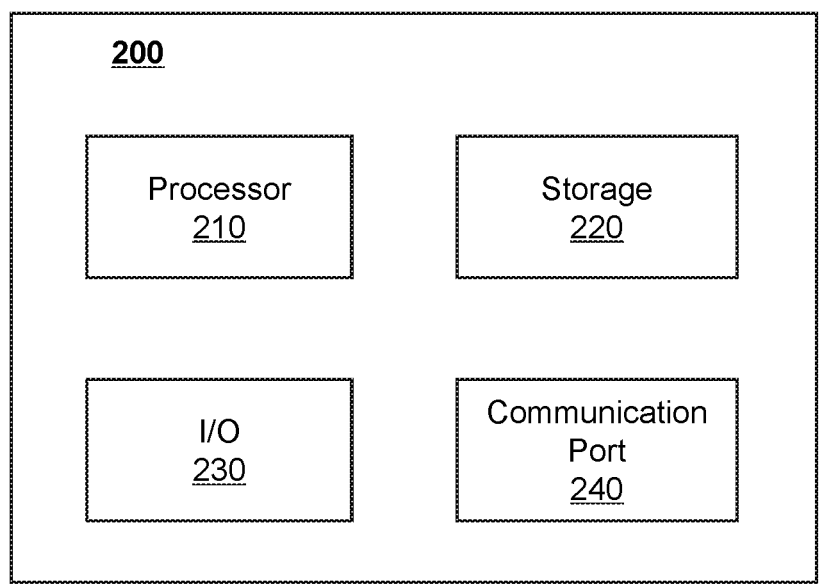
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a first image, or a second image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

Provided herein are systems and components for imaging and/or treatment, such as for disease diagnosis, treatment, or research purposes. In some embodiments, the systems may include an RT system, a computed tomography (CT) system (e.g., a multislice computed tomography (MSCT) system, a cone beam computed tomography (CBCT) system), an emission computed tomography (ECT) system, a positron emission tomography (PET) system, a single-positron emission tomography (SPECT), or the like, or any combination thereof. For illustration purposes, the disclosure describes systems and methods for image guided RT (IGRT).

In some embodiments, an IGRT system may include a first device (e.g., a treatment component) and a second device (e.g., an imaging component). The first device may deliver a radiation therapy treatment to a subject (e.g., a patient, an animal). The second device may acquire an image of the subject prior to the radiation therapy treatment, during the radiation therapy treatment, and/or after the radiation therapy treatment. The image may be used to determine and/or update a treatment plan for the subject. The treatment plan may describe how the radiation therapy treatment is planned to be performed on the subject, more specifically, how one or more beams are delivered to the subject during the radiation therapy treatment of the subject. In some embodiments, the first device may have a first isocenter, and the second device may have a second isocenter. In order to deliver an accurate radiation therapy treatment to the subject, it may be beneficial to determine a geometrical relationship between the first isocenter of the first device and the second isocenter of the second device. For example, in a stereotactic radiosurgery (SRS), the first isocenter of the first device may need to match closely to the second isocenter of the second device. It should be understood that, by establishing the position of the isocenter in an image, as long as the image axis orientations are known, the position of the isocenter is sufficient to determine the position of any point within the image, and vice versa. For this reason, the teachings herein apply to a more general interpretation of "isocenter" as any reference point within the imaging field-of-view of the imaging component (i.e., the second device, in the case where the first device is an RT system). In radiation therapy, such a reference point may be what is termed a "planning isocenter" (that may not correspond to a geometric rotational isocenter), as is further discussed below.

A Winston-Lutz based test is a conventional technique to determine the first isocenter of the first device (e.g., a treatment component including a megavoltage (MV) treatment source). Specifically, a ball bearing (BB) phantom may be placed on a couch (or otherwise within the radiation field of the first device), and imaged by the first device to determine a position of the first isocenter of the first device. The relationship between the isocenter of the first device and the isocenter of the second device may be established by moving the BB phantom (by a known amount) into the imaging field-of-view of the second device to determine a relative position of the second isocenter of the second device to the first isocenter of the first device. The relationship between the first isocenter and the second isocenter may be determined based on the position of the first isocenter and the position of the second isocenter (based on the imaged position of the BB in the second device relative to its image isocenter). For MV imaging, compared to a BB phantom made of a relatively low atomic number material, the use of a BB phantom made of a relatively high atomic number material (e.g., a tungsten BB phantom) may lead to a good contrast in the image. Therefore, a position of the tungsten BB phantom in the image may be identified easily, and accordingly the position of the first isocenter determined based on the position of the BB phantom may be more efficiently and/or accurately obtained. However, a BB phantom made of a relatively high atomic number material (e.g., a tungsten BB phantom) may lead to one or more streak artifacts in a kV image (e.g., a CT image), which may make the identification of a position of the BB phantom in the CT image difficult, and accordingly the position of the second isocenter determined based on the position of the tungsten sphere phantom may be inaccurate or even unobtainable.

Multi-BB phantoms may be provided to determine the geometrical relationship between the first isocenter of the first device and the second isocenter of the second device. Specifically, a first BB phantom made of a relatively high atomic number material (e.g., a tungsten BB phantom) may be used in a Winston-Lutz based test for the first device (e.g., by MV imaging) to determine a position of the first isocenter relative to the first BB phantom. A second BB phantom made of a relatively low atomic number material (e.g., a stainless-steel BB phantom) may be imaged (or used in a Winston-Lutz based test) for the second device (e.g., by kV imaging) to determine a position of the second isocenter relative to the second BB phantom. In order to determine the relationship between the first isocenter and the second isocenter, a position relationship between the second BB phantom and the first BB phantom may be determined. For example, the position of the second BB phantom relative to the couch may be the same as the position of the first BB phantom relative to the couch. However, repositioning the second BB phantom may introduce errors and take additional time.

An aspect of the present disclosure relates to systems and methods for isocenter calibration. A phantom including a first member and a second member with a fixed position relationship (e.g., connected by a coupling member) may be provided. According to some embodiments of the present disclosure, a processing device may acquire, using a first device, at least one first image of the first member of the phantom. The processing device may determine, based on the at least one first image, a first position relationship between a first isocenter of the first device and the first member (also referred to as a position of the first isocenter relative to the first member). The processing device may acquire, using a second device, at least one second image of the second member of the phantom. The processing device may determine, based on the at least one second image and the fixed position relationship between the first member and the second member, a second position relationship between a second isocenter of the second device and the first member (also referred to as a position of the second isocenter relative to the first member). The processing device may determine, based on the first position relationship and the second position relationship, a third position relationship between the first isocenter of the first device and the second isocenter of the second device.

Another aspect of the present disclosure relates to systems and methods for isocenter calibration. A phantom including a first member and a second member with a fixed position relationship (e.g., connected by a coupling member) may be provided. According to some embodiments of the present disclosure, a processing device may acquire, using a first device, a plurality of first images of the first member of the phantom. The processing device may determine, based on the plurality of first images, a position of a first isocenter of the first device. The processing device may acquire, using a second device, a plurality of second images of the second member of the phantom. The processing device may determine, based on the plurality of second images and the fixed position relationship between the first member and the second member, a position of a second isocenter of the second device. The processing device may determine, based on the position of the first isocenter and the position of the second isocenter, a position relationship between the first isocenter of the first device and the second isocenter of the second device.

Therefore, the position relationship between the first isocenter of the first device and the second isocenter of the second device may be determined using a single phantom including the first member and the second member with a fixed position relationship (e.g., connected by the coupling member). Errors introduced from unnecessary intermediate steps (e.g., positioning the phantom a second time, or using a second phantom) may be avoided, which may improve the accuracy and/or efficiency of the isocenter calibration process.

Additionally, in some embodiments, the first member may be made of a first material, and the second member may be made of a second material different from the first material. For instance, an atomic number of the first material may be higher than an atomic number of the second material. In some embodiments, the first member and the second member may be of different dimensions. For instance, an MV treatment system may be expected to have a geometric accuracy of 1 mm, so there would be little point in using a BB of, say 0.25 mm to perform a Winston-Lutz type test. Accordingly, a first radius of the first member may be larger than a second radius of the second member. Accordingly, the first member made of a relatively high atomic number material and with a relatively large radius may have a good contrast in the at least one first image acquired by MV imaging, and accordingly the first position relationship between the first isocenter of the first device and the first member may be determined with improved accuracy, precision and/or efficiency. The second member made of a relatively low atomic number material and with a relatively small radius may have a good resolution in the at least one second image acquired by kV imaging (for example, CT resolution may be typically significantly higher that MV system resolution), and streak artifacts in the at least one second image may be reduced. The position information of the second member in the at least one second image may be determined accurately, and the second position relationship between the second isocenter of the first device and the first member may also be determined accurately. The accuracy of the position relationship between the first isocenter and the second isocenter determined based on the first position relationship and the second position relationship may be improved.

Figure 1:
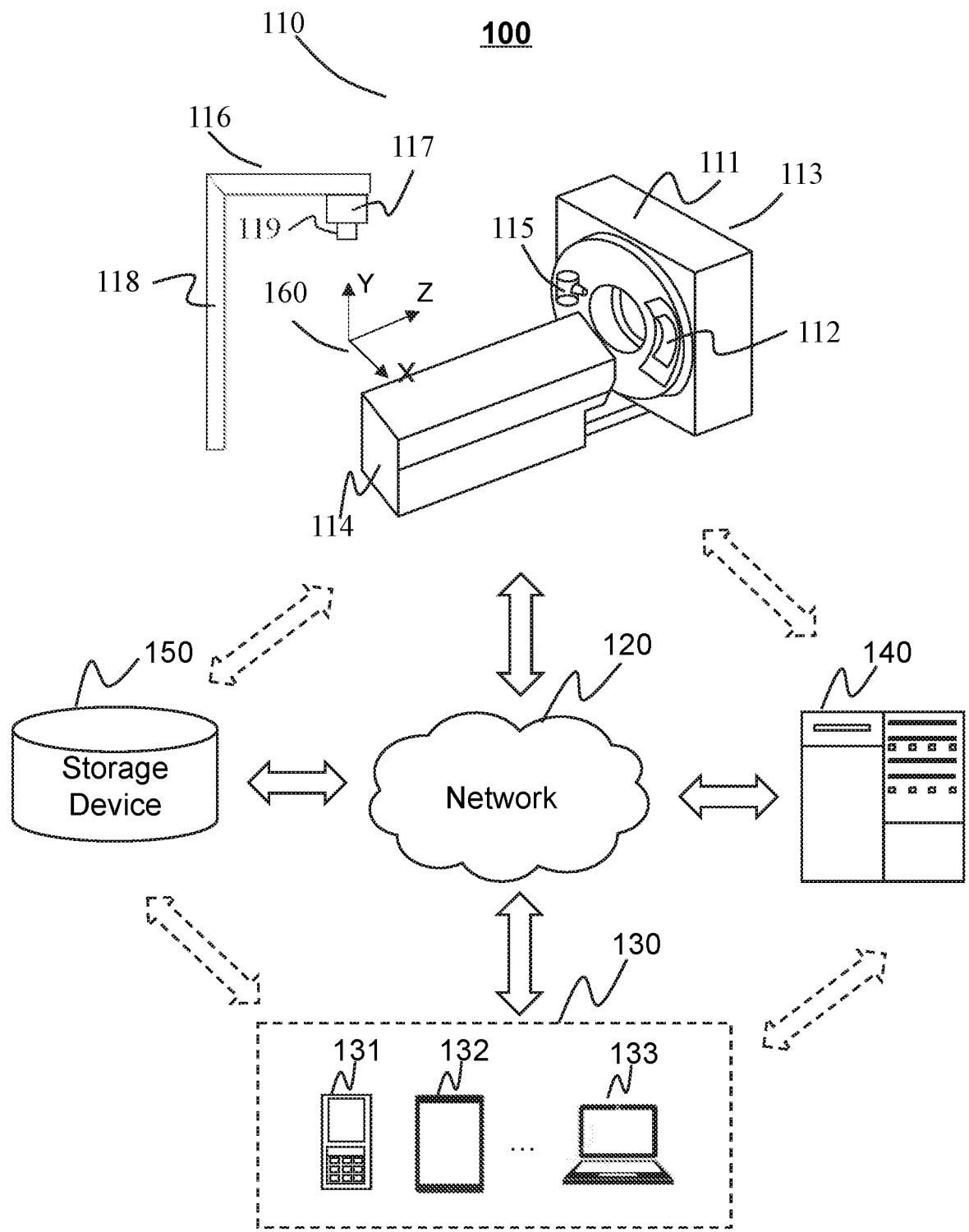
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include a radiation delivery device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the radiation delivery device 110 may be connected to the processing device 140 through the network 120 or directly as indicated by the bi-directional arrow in dotted lines linking the radiation delivery device 110 and the processing device 140. As another example, the storage device 150 may be connected to the radiation delivery device 110 through the network 120 or directly as indicated by the bi-directional arrow in dotted lines linking the storage device 150 and the radiation delivery device 110. As still another example, the terminal(s) 130 may be connected to the processing device 140 through the network 120 or directly as indicated by the bi-directional arrow in dotted lines linking the terminal(s) 130 and the processing device 140. As still another example, the terminal(s) 130 may be connected to the storage device 150 through the network 120 or directly as indicated by the bi-directional arrow in dotted lines linking the terminal(s) 130 and the storage device 150.

In some embodiments, the radiation delivery device 110 may be an RT device. The RT device may be configured to deliver a radiation therapy treatment for cancers and other conditions. For example, the RT device may deliver one or more radiation beams to a treatment region (e.g., a tumor) of a subject (e.g., a patient) for causing an alleviation of the subject's disease and/or symptoms. In some embodiments, the RT device may be a conformal radiation therapy device, an image guided radiation therapy (IGRT) device, an intensity modulated radiation therapy (IMRT) device, an intensity modulated arc therapy (IMAT) device, or the like. As illustrated in FIG. 1, the radiation delivery device 110 may include a first device 116 (also referred to as a treatment component), a second device 113 (also referred to as an imaging component), a couch 114, or the like.

The first device 116 may be configured to deliver a radiation therapy treatment to the subject. The subject may include any biological subject (e.g., a human being, an animal, a plant, or a portion thereof) and/or a non-biological subject (e.g., a phantom, structure/device to be non-destructively tested). The first device 116 may include a treatment head and a gantry 118. In some embodiments, the treatment head may include a treatment radiation source 117, a collimator 119, or the like. The treatment radiation source 117 may be configured to generate and emit a radiation beam toward the subject for treatment. The collimator 119 may be configured to control the shape of the radiation beam generated by the treatment radiation source 117. In some embodiments, the radiation beam emitted by the treatment radiation source 117 may include electrons, photons, or other types of radiation. In some embodiments, the energy of the radiation beam may have energy components exclusively or also in the megavoltage range (e.g., >1 MeV), and may be referred to as a megavoltage (MV) beam. In some embodiments, the treatment radiation source 117 may include a linear accelerator (LINAC) configured to accelerate electrons, ions, or protons.

In some embodiments, the treatment radiation source 117 may rotate around a rotation center (also be referred to as a first isocenter) during treatment. For example, the treatment radiation source 117 may include a LINAC, and the first isocenter of the treatment radiation source 117 may be a rotation isocenter of the LINAC.

In some embodiments, the first device 116 may be used to treat, as well as image (or referred to as scan), the subject. For example, the treatment radiation source 117 may be an MV treatment source that is configured to emit an MV beam toward the subject. The first device 116 may include a detector opposite to the treatment radiation source 117 configured to detect radiation emitted from its detection region. The MV treatment source in combination with the detector of the first device 116 may be used to perform MV imaging on the subject. Additionally, or alternatively, the first device 116 may include a radiation source in addition to the treatment radiation source 117. The additional radiation source may emit radioactive rays (e.g., a particle ray, a photon ray) to the subject. For example, the additional radiation source may be configured to emit X-rays, which may be used to perform a CBCT scan, an FBCT scan, or the like, on the subject. In some embodiments, the additional radiation source may be an MV radiation source for emitting an MV beam or a kilovoltage (kV) radiation source for emitting a kV beam (i.e., a radiation beam whose energy is within the kilovoltage range (e.g., >1 keV)). In some embodiments, the additional radiation source may be mounted on a same gantry (e.g., the gantry 118) as or a different gantry from the treatment radiation source 117.

In some embodiments, the treatment radiation source 117 may rotate around a rotation axis to be positioned at various gantry angles, such that the subject located in the couch 114 may be imaged and/or treated from a plurality of directions. Merely by way of example, the treatment radiation source 117 may be fixedly attached to the gantry 118, and a detector may be fixedly or flexibly attached to the gantry 118 opposite to the treatment radiation source 117. As used herein, a fixed attachment of component A (e.g., the treatment radiation source 117) to component B (e.g., the gantry 118) indicates that the component A does not move relatively to the component B when the component A and the component B are properly assembled and used as intended. As used herein, a flexible attachment of component A (e.g., the treatment radiation source 117) to component B (e.g., the gantry 118) indicates that the component A can move relatively to the component B when the component A and the component B are properly assembled and used as intended. When the gantry 118 rotates around a gantry rotation axis in a circular path, the treatment radiation source 117 and the detector attached on the gantry 118 may rotate along with the gantry 118, and the subject located in the couch 114 may be imaged and/or treated from a plurality of gantry angles. As used herein, a gantry angle relates to a position of a radiation source in the treatment radiation source 117 with reference to the first device 116. For example, a gantry angle may be an angle between a vertical direction (i.e., a Y axis direction of a coordinate system 160 as shown in FIG. 1) and a direction of a beam axis of a radiation beam emitted from the treatment radiation source 117 of the first device 116.

The second device 113 may be configured to acquire an image of the subject prior to a radiation therapy treatment, during the radiation therapy treatment, and/or after the radiation therapy treatment. In some embodiments, the second device may include a kilovoltage imaging source. For example, the second device 113 may include a computed tomography (CT) device (e.g., a cone beam computed tomography (CBCT) device, a multislice computed tomography (MSCT) device, a fan-beam computed tomography (FBCT) device), or the like, or any combination thereof. In some embodiments, the second device 113 may include an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof. For illustration purposes, the present disclosure takes a CT device as an exemplary second device 113. This is not intended to be limiting.

In some embodiments, the second device 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., X-ray photons, gamma-ray photons) emitted from an imaging region of the second device 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-row detector.

In some embodiments, the second device 113 may have the imaging region. As used herein, the imaging region of the second device 113 refers to a region that may be irradiated by radioactive rays emitted by the second device 113. The imaging region of the second device 113 may include a second isocenter of the second device 113. As used herein, the second isocenter of the second device 113 is defined as the axis of rotation of the second device 113, at the point where it intersects the plane of rotation.

In some embodiments, the second device 113 may be spaced by a distance from the first device 116. In some embodiments, the gantry 111 of the second device 113 and the gantry 118 of the first device 116 may share an axis of rotation. The subject may be positioned in different positions on the couch 114 for imaging and treatment. In some embodiments, the imaging radiation source 115 and the treatment radiation source 117 may be integrated as one radiation source to image and/or treat the subject. In some embodiments, the second device 113 and the first device 116 may share a same gantry. For example, the treatment radiation source 117 and the imaging radiation source 115 may be mounted on the gantry 111 of the second device 113. A subject may be placed on the couch 114 for treatment and/or imaging.

The couch 114 may be configured to support the subject to be treated and/or imaged. In some embodiments, the couch 114 may be movable between the first device 116 and the second device 113 along a Z-axis direction of the coordinate system 160 as shown in FIG. 1. In some embodiments, the couch 114 may be configured to rotate and/or translate along different directions so as to move the subject to a desired position (e.g., a treatment position under the first device 116 for treatment, an imaging position under the second device 113 for imaging). In some embodiments, the couch 114 may be six degrees of freedom. Six degrees of freedom (6DoF) may refer to the freedom of movement of a rigid body (e.g., the couch 114) in a three-dimensional space. Specifically, the couch 114 may be free to move forward/backward along the Z-axis, up/down along the Y-axis, left/right along the X-axis of the coordinate system 160 as shown in FIG. 1, combined with rotation about the X-axis (e.g., a roll rotation), the Y-axis (e.g., a pitch rotation), and the Z-axis (e.g., a yaw rotation).

The network 120 may include any suitable network that can facilitate the exchange of information and/or data for the RT system 100. In some embodiments, one or more components of the RT system 100 (e.g., the radiation delivery device 110, the terminal(s) 130, the processing device 140, the storage device 150, etc.) may communicate information and/or data with one or more other components of the RT system 100 via the network 120. For example, the processing device 140 may acquire at least one first image of a first member of a phantom from a first device (e.g., the first device 116) via the network 120. As another example, the processing device 140 may acquire at least one second image of a second member and a coupling member of a phantom from a second device (e.g., the second device 113) via the network 120. As another example, the processing device 140 may obtain user instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
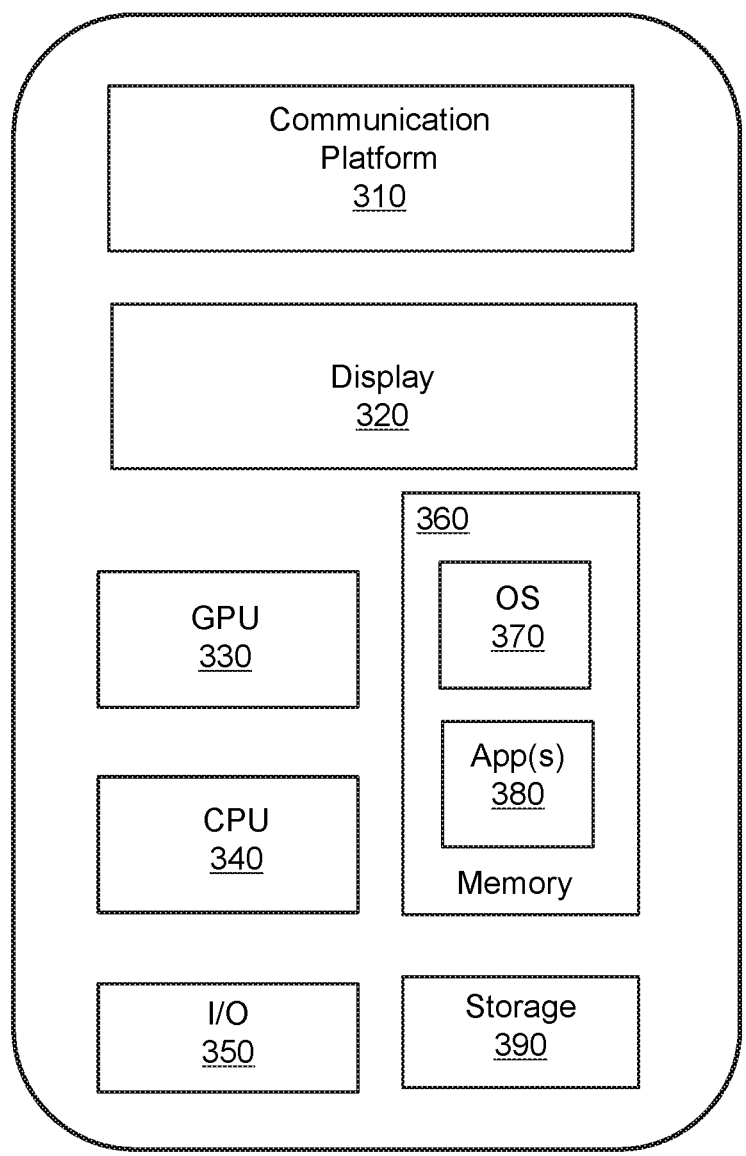
FIG. 3 is a schematic diagram illustrating exemplary hardware and/or software components of a mobile device according to some embodiments of the present disclosure.

The terminal(s) 130 may enable user interaction between a user and the RT system 100. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the radiation delivery device 110, the terminal(s) 130, and/or the storage device 150. For example, the processing device 140 may determine, based on at least one first image, a first position relationship between a first isocenter of a first device (e.g., the first device 116) and a first member of a phantom. As another example, the processing device 140 may determine, based on at least one second image, a second position relationship between a second isocenter of a second device (e.g., the second device 113) and a first member of a phantom. As still another example, the processing device 140 may determine, based on a first position relationship and a second position relationship, a third position relationship between a first isocenter of a first device (e.g., the first device 116) and a second isocenter of a second device (e.g., the second device 113). As a further example, the processing device 140 may determine, based on a plurality of first images, a position of a first isocenter of a first device (e.g., the first device 116). As still a further example, the processing device 140 may determine, based on a plurality of second images, a position of a second isocenter of a second device (e.g., the second device 113). As still a further example, the processing device 140 may determine, based on a position of a first isocenter and a position of a second isocenter, a position relationship between the first isocenter of a first device (e.g., the first device 116) and the second isocenter of a second device (e.g., the second device 113). In some embodiments, the processing device 140 may be a computer, a user console, a single server, a server group, etc. The server group may be centralized or distributed. In some embodiments, the processing device 140 may be local or remote. For example, the processing device 140 may access information stored in the radiation delivery device 110, the terminal(s) 130, and/or the storage device 150 via the network 120. As another example, the processing device 140 may be directly connected to the radiation delivery device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the processing device 140, the terminal(s) 130). One or more components of the RT system 100 may access the data and/or instructions stored in the storage device 150 via the network 120. In some embodiments, the storage device 150 may be directly connected to or communicate with one or more other components of the RT system 100 (e.g., the processing device 140, the terminal(s) 130). In some embodiments, the storage device 150 may be part of the processing device 140. In some embodiments, the storage device 150 may be connected to or communicate with the radiation delivery device 110 via the network 120, or at the backend of the processing device 140.

In some embodiments, a coordinate system may be provided for the RT system 100 to define a position of a component (e.g., an absolute position, a position relative to another component) and/or a movement of the component. For illustration purposes, the coordinate system 160 may include the X-axis, the Y-axis, and the Z-axis. The X-axis and the Z-axis shown in FIG. 1 may be horizontal, and the Y-axis may be vertical. As illustrated, a positive X direction along the X-axis may be from the left side to the right side of the couch 114 viewed from the direction facing the front of the radiation delivery device 110; a positive Y direction along the Y-axis may be from the lower part (or from the floor where the RT system 100 stands) to the upper part of the gantry 111; and a positive Z direction along the Z-axis may be the direction in which the couch 114 is moved from the outside into the RT system 100 viewed from the direction facing the front of the radiation delivery device 110.

It should be noted that the provided coordinate system 160 is illustrative, and not intended to limit the scope of the present disclosure. For example, the coordinate system 160 may only include two axes (e.g., the X-axis and the Y-axis). In addition, although the following descriptions discuss through various examples to determine a position of an entity by determining a coordinate of an entity in a certain coordinate system, it should be understood that the position of the entity may be determined by determining a coordinate of the entity in another coordinate system (e.g., a coordinate system that has a known transformation relationship with the certain coordinate system). For the convenience of descriptions, coordinates of an entity along an X-axis, a Y-axis, and a Z-axis in a coordinate system are also referred to as X-coordinates, Y-coordinates, and Z-coordinates of the entity in the coordinate system, respectively.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. Additionally or alternatively, two or more components of the RT system 100 may be integrated into a single component. A component of the RT system 100 may be implemented on two or more sub-components.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the radiation delivery device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input and/or output signals, data, information, etc. In some embodiments, the I/O 230 may enable user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of a mobile device 300 according to some embodiments of the present disclosure. In some embodiments, a terminal(s) 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
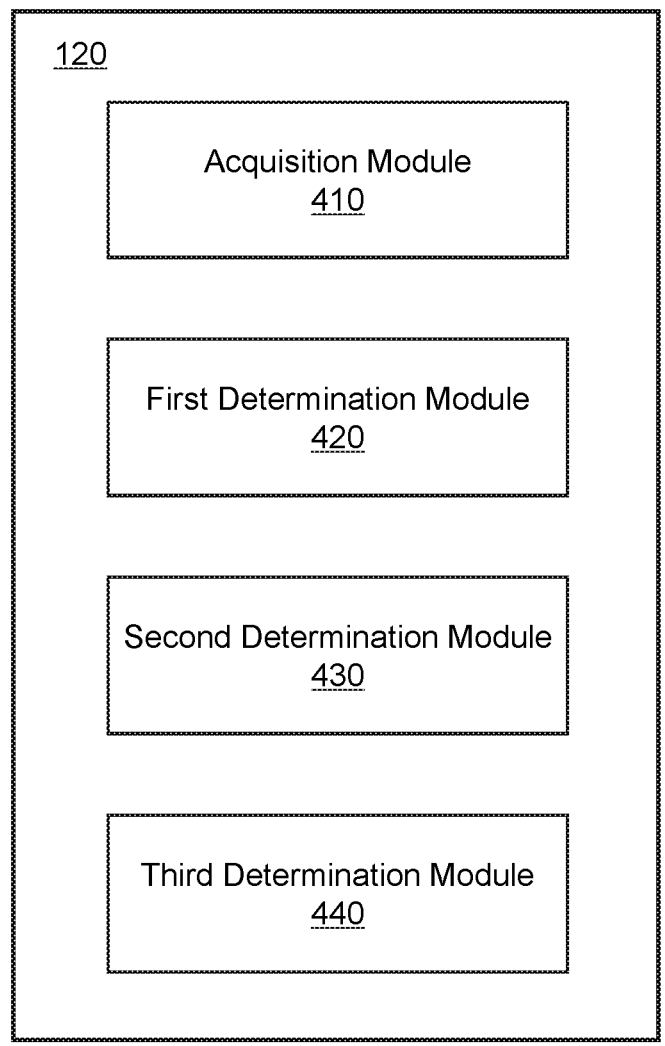
FIG. 4 is a block diagram illustrating an exemplary processing device according to some embodiments of the present disclosure.

FIG. 4 is a block diagram illustrating an exemplary processing device according to some embodiments of the present disclosure. As shown in FIG. 4, the processing device 140 may include an acquisition module 410, and a first determination module 420, a second determination module 430, and a third determination module 440.

The acquisition module 410 may be configured to acquire data and/or information associated with the RT system 100. The data and/or information associated with the RT system 100 may include an image of a phantom, a first relationship between a first isocenter of a first device and the phantom, a second relationship between a second isocenter of a second device and the phantom, or the like, or any combination thereof. For example, the acquisition module 410 may acquire, using a first device (e.g., the first device 116), at least one first image of a first member of a phantom. As another example, the acquisition module 410 may acquire, using a second device, at least one second image of a second member (and a coupling member) of a phantom. In some embodiments, the acquisition module 410 may obtain the data and/or the information associated with the RT system 100 from one or more components (e.g., the terminal device 130, the storage device 150, the radiation delivery device 110) of the RT system 100 via the network 120.

The first determination module 420 may be configured to determine a first position relationship between a first isocenter of a first device and a phantom. In some embodiments, the first determination module 420 may determine a first position relationship between a first isocenter of a first device and a first member of a phantom based on at least one first image of a first member of a phantom. More descriptions for determining the first position relationship may be found elsewhere in the present disclosure (e.g., FIG. 6 and the descriptions thereof). In some embodiments, the first determination module 420 may determine a position of a first isocenter of a first device based on a plurality of first images of a first member of a phantom. More descriptions for determining the first isocenter of the first device may be found elsewhere in the present disclosure (e.g., FIG. 8 and the descriptions thereof).

The second determination module 430 may be configured to determine a second position relationship between a second isocenter of a second device and a phantom. In some embodiments, the second determination module 430 may determine a second position relationship between a second isocenter of a second device and a first member of a phantom based on at least one second image of a second member of a phantom and a fixed position relationship between the first member and the second member. For example, the second determination module 430 may determine a second position relationship between a second isocenter of a second device and a first member of a phantom based on at least one second image of a second member and a coupling member of a phantom. More descriptions for determining the second position relationship may be found elsewhere in the present disclosure (e.g., FIG. 7 and the descriptions thereof). In some embodiments, the second determination module 430 may determine a position of a second isocenter of a second device based on a plurality of second images of a second member of a phantom and a fixed position relationship between the first member and the second member. For example, the second determination module 430 may determine a position of a second isocenter of a second device based on a plurality of second images of a second member and a coupling member of a phantom. More descriptions for determining the second isocenter of the second device may be found elsewhere in the present disclosure (e.g., FIG. 8 and the descriptions thereof).

The third determination module 440 may be configured to determine a third position relationship between a first isocenter of a first device and a second isocenter of a second device. In some embodiments, the third determination module 440 may determine a third position relationship between a first isocenter of a first device and a second isocenter of a second device based on a first relationship between the first isocenter of the first device and the phantom and the second relationship between the second isocenter of the second device and the phantom. More descriptions for determining the third position relationship may be found elsewhere in the present disclosure (e.g., FIG. 5 and the descriptions thereof). In some embodiments, the third determination module 440 may determine a position relationship between a first isocenter of a first device and a second isocenter of a second device based on a position of the first isocenter and a position of the second isocenter. More descriptions for determining the position relationship may be found elsewhere in the present disclosure (e.g., FIG. 8 and the descriptions thereof).

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. For instance, at least two of the first determination module 420, the second determination module 430, and the third determination module 440 may be one module. However, those variations and modifications also fall within the scope of the present disclosure.

Figure 5:
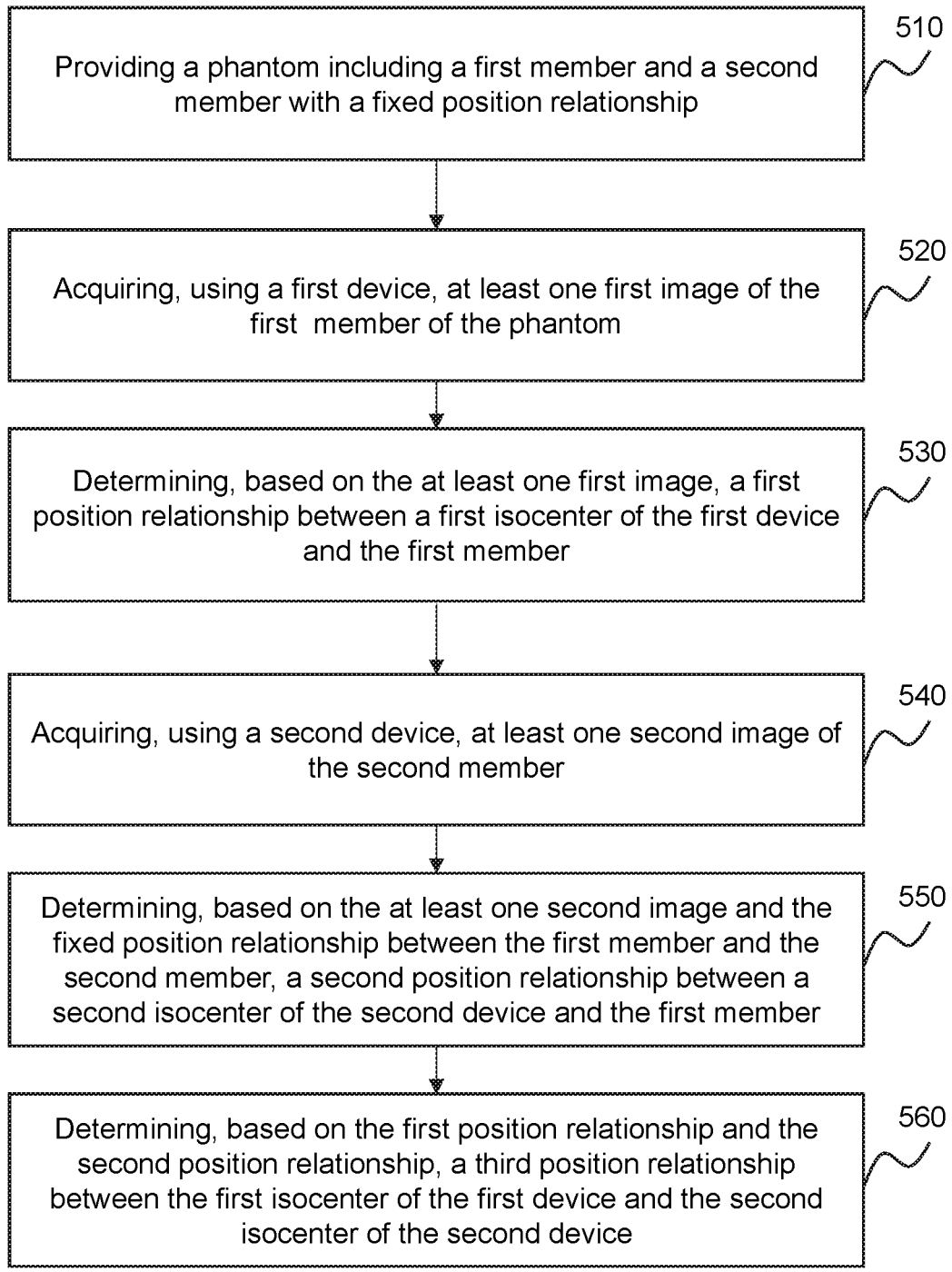
FIG. 5 is a flowchart illustrating an exemplary process for determining a position relationship between a first isocenter of a first device and a second isocenter of a second device according to some embodiments of the present disclosure.

FIG. 5 is a flowchart illustrating an exemplary process for determining a position relationship between a first isocenter of a first device and a second isocenter of a second device according to some embodiments of the present disclosure. In some embodiments, process 500 may be executed by the RT system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 510, a phantom including a first member and a second member with a fixed position relationship may be provided.

As used herein, a fix position relationship between the first member and the second member refers to that if a position of the first member (or a position of the second member) is known, the position of the second member (or the position of the first member) can be determined. In some embodiments, the first member and the second member may be connected by a coupling member.

The phantom may be configured to determine a position relationship between a first isocenter of a first device (e.g., the first device 116) and a second isocenter of a second device (e.g., the second device 113). In some embodiments, the phantom may include the first member, the second member, and the coupling member. The first member and the second member may be connected by the coupling member. In some embodiments, the first member may be imaged by the first device and configured to determine a position of the first isocenter. The second member may be imaged by the second device and configured to determine a position of the second isocenter. The coupling member may be configured to determine a fix position relationship between the first member and the second member.

The phantom may have a specific shape and a specific size. For example, the first member and the second member may have a pyramid shape, a sphere shape, a cube shape, or the like. The shape of the first member may be the same as or different from the shape of the second member. For example, the first member may be a sphere, and the second member may be a cube. As another example, the first member and the second member may both be spheres. In some embodiments, the size of the phantom may affect a contrast of the phantom and/or a resolution of the phantom in a reconstructed image of the phantom acquired by the first device or the second device. Take the first member or the second member is a sphere as an example, the larger the radius of the sphere, the greater the contrast of the sphere in the reconstructed image, and the lower the resolution of the sphere in the reconstructed image. A first radius of the first member may be the same as or different from a second radius of the second member. In some embodiments, the first radius of the first member may be similar to an intrinsic spatial resolution of the first device. In some embodiments, the second radius of the second member may be similar to an intrinsic spatial resolution of the second device. In some embodiments, compared with the first device (e.g., a MV treatment device), the second device (e.g., a CT device) may have a higher intrinsic spatial resolution, and/or contrast resolution. Accordingly, the first radius of the first member may be larger than the second radius of the second member. For example, the first radius of the first member may be 6.5 mm, and the second radius of the second member may be 0.5 mm.

In some embodiments, the first member may be made of a first material, and the second member may be made of a second material. In some embodiments, the first material may be the same as the second material. For example, the first material and the second material may be stainless-steel. In some embodiments, the first material may be different from the second material. The first material and the second material may be determined based on types of the first device and the second device. For illustration purposes, the first device may be a treatment component including a MV treatment source (also referred to as a MV treatment component), and the second device may be a kV imaging component (e.g., a CBCT device, an MSCT device). An atomic number of the first material may be higher than an atomic number of the second material. In some embodiments, the first material may be a high atomic number material, and the second material may be a low atomic number material. That is, the first material may be composed of an element with an atomic number greater than 18, and the second material may be composed of an element with an atomic number lower than 18. For example, the first material may include a metal, such as iron, gold, tungsten, or the like, or an alloy thereof, or any combination thereof. The second material may include plastic, stainless steel, or the like, or any combination thereof. Accordingly, the first member made of the high atomic number material may have a good contrast in MV imaging, which may make the determination of the position of the first isocenter based on an image generated in the MV imaging more accurate and easier. Compared with the first member made of the high atomic number material, the second member made of the low atomic number material may cause less streak artifact in kV imaging, which may make the determination of the position of the second isocenter based on an image generated in the KV imaging accurately and easily.

In some embodiments, the first member and the second member may be separated by a distance. As used herein, the distance between the first member and the second member refers to a shortest distance between the first member and the second member. For example, if the first member and the second member are spheres, the distance between the first member and the second member may be a shortest distance between edges of the two spheres. In order to determine the position of the first isocenter and the position of the second isocenter accurately, the first member and the second member may be placed and imaged by the first device near the first isocenter, and then be placed and imaged by the second device near the second isocenter. That is, the distance between the first member and the second member may be as short as possible (e.g., less than a first threshold). If the distance between the first member and the second member is greater than the first threshold, an axis connecting a center point of the first member and a center point of the second member may form an angle with respect to an axis joining the first isocenter and the second isocenter due to imprecise placement, and at least one of the first member and the second member may be offset significantly from a corresponding isocenter in an axial plane. On the other hand, if the distance between the first member and the second member is too short (e.g., less than a second distance threshold), artifacts caused by the first member made of the high atomic number material may affect the determination of position information of the second member in a reconstructed image of the phantom acquired by the second device. Therefore, the distance between the first member and the second member may satisfy a specific condition (e.g., less than the first distance threshold and greater than the second distance threshold), such that the artifacts caused by the first member made of the high atomic number material do not affect the determination of position information of the second member in the reconstructed image of the phantom, and the first member and the second member may both be placed and imaged near the first isocenter and the second isocenter, respectively. For illustration purposes, if the first member is a tungsten sphere with the first radius of 6.5 mm, and the second member is a plastic sphere with the second radius of 3 mm, the distance between the first member and the second member may be 3 mm.

In some embodiments, the coupling member may be a solid rod or an annular rod. A cross-section of the coupling member along its longitudinal axis may have an outer contour having the shape of a circle, an ellipse, a square, a rectangle, etc. As used herein, the longitudinal axis of the coupling member of the phantom is along the direction in which the first member and the second member are spaced apart. The coupling member may be made of a third material. The third material may be the same as or different from the first material and/or the second material. Merely by way of example, the coupling member may be a solid stainless-steel rod with a cross-sectional diameter of 3 mm. The configuration of the coupling member may facilitate the measurement of a lateral displacement of the couch 114 along the X-axis during a movement of the couch 114 as described elsewhere in the present disclosure.

Figure 9A:
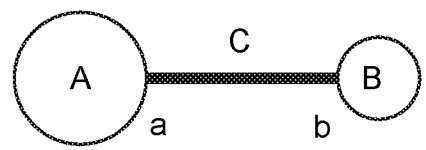
FIG. 9A is a schematic diagram illustrating an exemplary phantom according to some embodiments of the present disclosure.
Figure 9B:
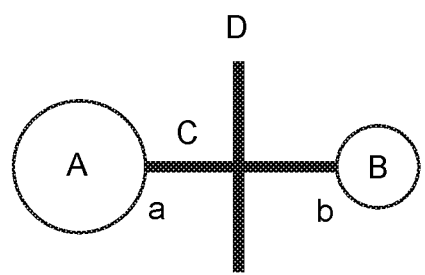
FIG. 9B is a schematic diagram illustrating an exemplary phantom according to some embodiments of the present disclosure.
Figure 9C:
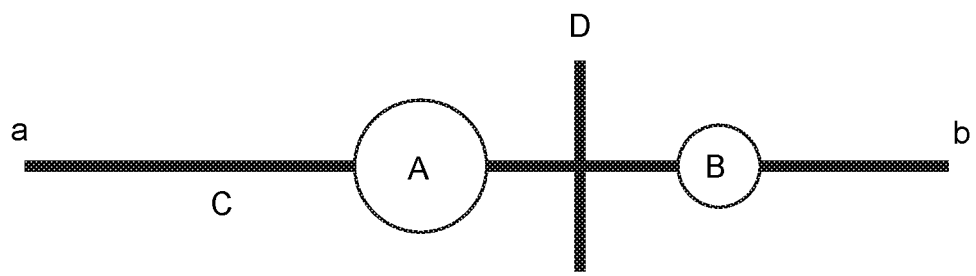
FIG. 9C is a schematic diagram illustrating an exemplary phantom according to some embodiments of the present disclosure.

In some embodiments, the coupling member may have a first end corresponding to the first member and a second end corresponding to the second member. As used herein, an end of the coupling member corresponding to a member of a two-member phantom refers to that the end of the coupling member is closer to the member than to the other member of the phantom. In some embodiments, the first end may be connected to the first member, and the second end may be connected to the second member, as illustrated in FIG. 9A. In some embodiments, at least one end of the first end or the second end of the coupling member may extend beyond a corresponding member of the phantom. For example, the first end may extend beyond the first member, and the second end may extend beyond the second member, as illustrated in FIG. 9C.

In some embodiments, the phantom may further include a cross member disposed at an angle with the coupling member. The configuration of the cross member may facilitate the measurement of a longitudinal displacement of the couch 114 along the Z-axis during a movement of the couch 114, as well as roll rotation of the couch 114, as described elsewhere in the present disclosure. The position of the cross member on the coupling member may be such that it is not obscured by artifacts caused by the first member made of the high atomic number material in a reconstructed image of the phantom acquired by the second device. For example, the cross member may be disposed at a center point on the coupling member between the first member and the second member and perpendicular to the coupling member, as illustrated in FIGS. 9B and 9C. More descriptions of the phantom may be found elsewhere in the present disclosure (e.g., FIGS. 9A, 9B, 9C, and the descriptions thereof).

In some embodiments, the first member, the second member, the coupling member, and the cross member may be an integrally formed component. In some embodiments, the coupling member may be connected to the first member, the second member, and/or the cross member via a chemical (e.g., an adhesive), a mechanical component (e.g., a nail, a screw, a nut), or the like, or any combination thereof.

In 520, the processing device 140 (e.g., the acquisition module 410) may acquire, using the first device (e.g., the first device 116), at least one first image of the first member of the phantom.

The phantom may be placed at a first position with respect to the first device before the acquisition of the at least one first image. For example, the phantom may be placed at the first position such that the first member of the phantom may be located at or near a specific position, and an extending direction of the coupling member may be parallel with or substantially parallel with the Z-axis in the coordinate system 160 as described in FIG. 1. As used herein, the extending direction of the coupling member refers to a direction from the first end (or the second end) to the second end (or the first end) of the coupling member. The specific position may be a position in the vicinity of the first isocenter of a treatment radiation source (e.g., the treatment radiation source 117) of the first device. For example, a distance between specific position and the first isocenter may be less than 3 mm. Additionally or alternatively, the specific position may be a reference position the position of which is known in the coordinate system 160 of the RT system 100. In some embodiments, the specific position may be determined based on a light field crosshair or room lasers. In some embodiments, the RT system 100 may include a room laser system. The room laser system may provide a laser line or a crosshair used for positioning. Merely by way of example, the first member may be placed at the specific position to align the center of the first member with the center of the light field crosshair or the room lasers. In some embodiments, the extending direction of the coupling member may be aligned with the Z-axis based on the room lasers. Additionally or alternatively, the extending direction of the coupling member may be aligned with the Z-axis. The alignment may be checked using a leveling device or a level indicator (e.g., a spirit level) placed on the phantom.

In some embodiments, if the phantom includes the cross member disposed on the coupling member and perpendicular to the coupling member, an extending direction of the cross member may be parallel with or substantially parallel with the X-axis in the coordinate system 160 as described in FIG. 1. In some embodiments, the phantom may be placed at a fixed or approximately fixed position on the couch during the acquisition of the at least one first image. When the phantom is at a certain position, the certain position (e.g., the first position) of the phantom may be represented by a corresponding position (e.g., an encoder position) of the couch. Merely by way of example, the first position may be represented by a known encoder position of the couch measured by a position encoder of the couch. The phantom may be manually placed at the first position by a user of the RT system 100. Additionally or alternatively, the phantom may be placed at the first position by one or more components of the RT system 100 automatically.

In some embodiments, the at least one first image may include a two-dimensional (2D) image, a three-dimensional (3D) image, a series of images (e.g., a series of 2D images, a series of 3D images) over time, and/or any related image data (e.g., scan data, projection data). For example, the first image may be a projection image (e.g., a MV portal image) of the phantom acquired from a specific gantry angle. For example, a treatment radiation source (e.g., the treatment radiation source 117) may be fixedly attached to a gantry (e.g., the gantry 118), while a detector may be fixedly or flexibly attached to the gantry (e.g., the gantry 118) opposite to the treatment radiation source. When the gantry 118 rotates around a rotation axis, the treatment radiation source 117 and the detector may rotate along with the gantry 118, and the phantom may be imaged from a plurality of gantry angles. In some embodiments, the phantom may be imaged every time the gantry angle changes 90° for a total change of 360°.

In some embodiments, the processing device 140 may obtain the at least one first image from the first device periodically (e.g., every second, every 2 seconds, every 5 seconds, every 10 seconds) or in real time. In some embodiments, the first device may transmit the at least one first image to a storage device (e.g., the storage device 150) periodically (e.g., every second, every 2 seconds, every 5 seconds, every 10 seconds) or in real time via the network 120. Further, the processing device 140 may access the storage device and retrieve the at least one first image.

In 530, the processing device 140 (e.g., the first determination module 420) may determine, based on the at least one first image, a first position relationship between a first isocenter of the first device and the first member.

As used herein, the first position relationship between a first isocenter of the first device and the first member refers to a position of the first isocenter relative to the first member. In some embodiments, the processing device 140 may determine position information of the first isocenter based on a radiation field center in each of the at least one first image. The processing device 140 may determine position information of the first member in the each of the at least one first image. The processing device 140 may determine the first position relationship based on the position information of the first isocenter and the position information of the first member in the each of the at least one first image. More descriptions for determining the first position relationship may be found elsewhere in the present disclosure (e.g., FIG. 6 and the descriptions thereof).

In 540, the processing device 140 (e.g., the acquisition module 410) may acquire, using a second device, at least one second image of the second member of the phantom.

In some embodiments, the processing device 140 may cause the couch (e.g., the couch 114) to move the phantom from the first position to a second position with respect to the second device after the acquisition of the at least one first image and before the acquisition of the at least one second image. In some embodiments, the couch may move along a moving path to reach to the second position. The moving path may be parallel with or substantially parallel with the Z-axis as described in FIG. 1.

In some embodiments, the second device may be an MSCT. After the phantom is placed at the second position, the extending direction of the coupling member may be parallel with or substantially parallel with a direction along which the couch may be fed into a CT bore (e.g., the Z-axis) during the acquisition of the at least one second image. In some embodiments, the second device may be a CBCT device. The phantom may be placed at the second position such that the second member of the phantom may be located at or near a specific position. The specific position may be a position in the vicinity of the second isocenter of the second device. For example, a distance between the specific position and the second isocenter may be less than 3 mm. Additionally or alternatively, the specific position may be a reference position that is known in the coordinate system 160 of the RT system 100. In some embodiments, the specific position may be determined based on a light field crosshair or room lasers as described elsewhere in the present disclosure. In some embodiments, the specific position may be determined based on one or more intermediate images (e.g., CT images). For example, the phantom may be imaged by the second device to generate an intermediate image. A distance between the second member and a center point of the intermediate image may be determined. The position of the second member may be adjusted based on the distance so that the second member is located in the vicinity of the center point of the intermediate image.

In some embodiments, the phantom supported on the couch may be moved from the first position to the second position by a user of the RT system 100 manually, or by one or more components of the RT system 100 automatically.

In some embodiments, the at least one second image may include a 2D image, a 3D image, a series of image (e.g., a series of 2D images, a series of 3D images) over time, and/or any related image data (e.g., scan data, projection data). For example, the at least one second image may be a 3D image relating to the second member and the coupling member of the phantom. Alternatively, the at least one second image may be a plurality of 2D images (e.g., slice images) relating to the second member and the coupling member of the phantom, wherein the combination of the 2D images may be regarded as a 3D image of the second member and the coupling member of the phantom.

In some embodiments, the processing device 140 may direct the second device to perform a scan (e.g., a CBCT scan, an MSCT scan) on the phantom to generate the at least one second image. The field of view (FOV) of the second device during the scan may cover the second member, and at least a portion of the coupling member. In some embodiments, the processing device 140 may obtain the at least one second image from the second device periodically (e.g., every second, every 2 seconds, every 5 seconds, every 10 seconds) or in real time. In some embodiments, the second device may transmit the at least one second image to a storage device (e.g., the storage device 150) periodically (e.g., every second, every 2 seconds, every 5 seconds, every 10 seconds) or in real time via the network 120. Further, the processing device 140 may access the storage device and retrieve the at least one second image.

In 550, the processing device 140 (e.g., the second determination module 430) may determine, based on the at least one second image and the fixed position relationship between the first member and the second member, a second position relationship between a second isocenter of the second device and the first member.

As used herein, the second position relationship between the second isocenter of the second device and the first member refers to a position of the second isocenter relative to the first member. In some embodiments, the processing device 140 may determine position information of the second member in each of the at least one second image. The processing device 140 may determine position information of the first member in the each of the at least one second image based on the position information of the second member in the each of the at least one second image and the fixed position relationship between the first member and the second member. The processing device 140 may determine an image center in the each of the at least one second image. The processing device 140 may determine the second position relationship based on the position information of the first member in the each of the at least one second image and the image center in the each of the at least one second image. More descriptions for determining the second position relationship may be found elsewhere in the present disclosure (e.g., FIG. 7 and the descriptions thereof).

In 560, the processing device 140 (e.g., the third determination module 440) may determine, based on the first position relationship and the second position relationship, a third position relationship between the first isocenter of the first device and the second isocenter of the second device.

In some embodiments, based on the at least one first image, the processing device 140 may determine a position of the first isocenter relative to the first member when the phantom is at the first position (i.e., during the acquisition of the at least one first image). Based on the at least one second image, the processing device 140 may determine a position of the second isocenter relative to the first member when the phantom is at the second position (i.e., during the acquisition of the at least one second image). Further, the processing device 140 may determine the third position relationship based on the position of the first isocenter relative to the first member and the position of the second isocenter relative to the first member. For example, the processing device 140 may determine first coordinates of the first isocenter based on first coordinates of the first member when the phantom is at the first position and the first position relationship. The processing device 140 may determine second coordinates of the second isocenter based on second coordinates of the first member when the phantom is at the second position and the second position relationship. The processing device 140 may determine the third position relationship based on the first coordinates of the first isocenter and the second coordinates of the second isocenter.

In some embodiments, the processing device 140 (e.g., the third determination module 440) may determine whether the third position relationship satisfies a preset condition. The present condition may be manually set by a user of the RT system 100, or determined by one or more components of the RT system 100 according to different situations. For example, the processing device 140 may determine whether a distance between the first isocenter and the second isocenter satisfies the preset condition (e.g., less than a distance threshold). In response to determining that the third position relationship does not satisfy the preset condition, the processing device 140 may determine that one of the first device or the second device needs to be adjusted. For example, if a radiation beam of the first device is not aligned with the phantom, a beam alignment procedure may be performed. As another example, if the mechanics of the first device or the second device (e.g., a mechanical structure of the first device or the second device) are imprecise, a mechanical alignment procedure may be performed. As still another example, if there is an error in a reported moving distance of the couch, a mechanical calibration procedure of the couch may be performed. As a further example, if there is an angular deviation of the couch during the movement of the couch, a couch moving direction may be calibrated.

In some embodiments, in response to determining that the third position relationship does not satisfy the preset condition, the processing device 140 may generate a reminder. The reminder may be in the form of text, voice, an image, a video, a haptic alert, or the like, or any combination thereof. For example, the processing device 140 may transmit the reminder to a terminal device (e.g., the terminal device 130) of a user (e.g., a doctor) of the RT system 100. The terminal device may output the reminder to the user. Optionally, the user may input an instruction or information in response to the reminder. Merely by way of example, the user may manually adjust the first device and/or the second device. As another example, in response to determining that the third position relationship does not satisfy the preset condition, the first device and/or the second device may be adjusted automatically.

In some embodiments, the isocenter calibration process 500 may be performed before a radiation therapy treatment to a subject, as a general quality assurance (QA) procedure, as a general system geometry integrity check, or as a treatment device/imaging device isocenter consistency check.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. Additionally, the order of the process 500 may not be intended to be limiting. For example, operations 540 and 550 may be performed before operations 520 and 530. The processing device 140 may determine the second position relationship between the second isocenter of the second device and the first member. The processing device 140 may then determine the first position relationship between the first isocenter of the first device and the first member.

In some embodiments, the RT system 100 may include the first device (e.g., the first device 116), the second device (e.g., the second device 113), and a third device. The third device may include a PET device or a SPECT device. The phantom may further include a third member placed on the coupling member (or the cross member) of the phantom. A PET tracer (or a SPECT tracer) may be injected into the third member, and the third member may be imaged by the third device. In some embodiments, for the PET device, the PET tracer may include carbon-11, nitrogen-13, oxygen-15, fluorine-18F, Gallium-68, or the like, or any combination thereof. For the SPECT device, the SPECT tracer may include technetium-99, iodine-123, indium-111, iodine-131, cobalt-57, barium-133, or the like, or any combination thereof. A sealed radiation source or other radiation source containing a PET- and/or SPECT-visible isotope may be used as a "tracer" in some embodiments.

In some embodiments, the phantom including the first member, the second member, the third member, and the coupling member may be configured to determine a position relationship between the first isocenter of the first device, the second isocenter of the second device, and a third isocenter of the third device. As used herein, an isocenter of the PET device (or the SPECT device) refers to a center of a reconstructed PET image (or a reconstructed SPECT image), or a reference point the position of which is known in the reconstructed PET image (or the reconstructed SPECT image) or in a physical imaging space. For example, the processing device 140 may determine a position relationship between the first isocenter of the first device and the third isocenter of the third device using the first member, the third member, and the coupling member of the phantom as described in process 500. As another example, the processing device 140 may determine a position relationship between the second isocenter of the second device and the third isocenter of the third device using the second member, the third member, and the coupling member of the phantom as described in process 500.

In some embodiments, the PET imageable tracer/isotope (or the SPECT tracer/isotope) may be present in the phantom. For example, the PET-visible tracer/isotope (or the SPECT tracer/isotope) may be injected/attached into/onto the first member of the phantom. The first member with the PET tracer/isotope (or the SPECT tracer/isotope) may be imaged by the first device and the third device. In some embodiments, the PET-visible tracer/isotope (or the SPECT tracer/isotope) may be injected/attached into/onto the second member of the phantom. The second member with the PET tracer/isotope may be imaged by the second device and the third device. The processing device 140 may determine the position relationship between the first isocenter of the first device, the second isocenter of the second device, and the third isocenter of the third device using the phantom.

In some embodiments, the first device may be the PET device (or the SPECT device), and the second device may include a CT device. The PET tracer (or the SPECT tracer) may be injected/attached into/onto the first member of the phantom to determine a position relationship between an isocenter of the PET device (or the SPECT device) and an isocenter of the CT device as described in process 500.

In some embodiments, the processing device 140 may determine one or more rotation components of the couch during the movement of the couch between the first position and the second position. The rotation component may include a roll rotation component, a pitch rotation component, a yaw rotation component, or the like, or any combination thereof. As used herein, the roll rotation component refers to an angle offset of the couch from the X-axis during the movement of the couch. As used herein, the pitch rotation component refers to an angle offset of the couch from the Y-axis during the movement of the couch. As used herein, the yaw rotation component refers to an angle offset of the couch from the Z-axis during the movement of the couch. For example, the processing device 140 may determine the roll rotation component based on an angle offset of the extending direction of the cross member from the X-axis during the movement of the couch. The processing device 140 may determine the pitch rotation component based on an angle offset of the extending direction of the cross member from the Y-axis during the movement of the couch. The processing device 140 may determine the yaw rotation component based on an angle offset of the extending direction of the coupling member from the Z-axis during the movement of the couch.

In some embodiments, a lateral displacement (also referred to as a translation component) of the couch along the X-axis during the movement of the couch between the first position and the second position may be determined based on position information of the coupling member when the phantom is located at the first position, and position information of the coupling member when the phantom is located at the second position. In some embodiments, the lateral displacement of the couch may be determined based on X-coordinate(s) of one or more points of the coupling member when the phantom is located at the first position and X-coordinate(s) of the same one or more points of the coupling member when the phantom is located at the second position in the coordinate system 160 as shown in FIG. 1. For instance, the lateral displacement of the couch may be determined by determining a difference (e.g., by subtraction) between the X-coordinate of a point A of the coupling member when the phantom is located at the first position and the X-coordinate of the point A of the coupling member when the phantom is located at the second position in the coordinate system 160 as shown in FIG. 1. As another example, the lateral displacement of the couch may be determined by determining a difference (e.g., by subtraction) between an average X-coordinate of various points of the coupling member when the phantom is located at the first position and the average X-coordinate of the various points of the coupling member when the phantom is located at the second position in the coordinate system 160 as shown in FIG. 1.

In some embodiments, a longitudinal displacement (also referred to as a translation component) of the couch along the Z-axis during the movement of the couch between the first position and the second position may be determined based on position information of the cross member when the phantom is located at the first position, and position information of the cross member when the phantom is located at the second position. In some embodiments, the longitudinal displacement of the couch may be determined based on Z-coordinate(s) of one or more points of the cross member when the phantom is located at the first position and Z-coordinate(s) of the same one or more points of the cross member when the phantom is located at the second position in the coordinate system 160 as shown in FIG. 1. For instance, the longitudinal displacement of the couch may be determined by determining a difference (e.g., by subtraction) between the Z-coordinate of a point B of the cross member when the phantom is located at the first position and the Z-coordinate of the point B of the cross member when the phantom is located at the second position in the coordinate system 160 as shown in FIG. 1. As another example, the longitudinal displacement of the couch may be determined by determining a difference (e.g., by subtraction) between an average Z-coordinate of various points of the cross member when the phantom is located at the first position and the average Z-coordinate of the various points of the cross member when the phantom is located at the second position in the coordinate system 160 as shown in FIG. 1.

In some embodiments, a light emitter or a reflector may be placed on the phantom to calibrate an optical system in the RT system 100. The optical system may include a Varian real-time position management (RPM) system, an Accuray Synchrony respiratory tracking system, or the like. The Varian RPM system and the Synchrony respiratory tracking system may be used to track a movement (e.g., a respiratory motion) of the subject during the radiation treatment. For example, the Varian RPM system may be used in order to control a radiation beam on/off in case there are any unexpected movements of the subject during the radiation treatment. The Synchrony respiratory tracking system may continuously (e.g., periodically) synchronize a treatment beam delivery to a motion of a target of the subject that is undergoing the respiration motion. For example, an infrared radiation (IR) camera and/or a passive IR reflector may be placed on the phantom to calibrate the Varian RPM system. As another example, an IR camera and/or an active IR light-emitting diode (LED) light may be placed on the phantom to calibrate the Synchrony respiratory tracking system (e.g., a Synchrony vest).

In some embodiments, the processing device 140 may verify a moving distance of the couch measured by one or more position encoders during the movement of the couch between the first position and the second position. In some embodiments, the couch encoder position may be used to measure the moving distance that the couch travels between the first position and the second position, which may be vulnerable to inaccuracies caused by, e.g., an incorrect calibration of the position encoder or effects such as a backlash. An actual moving distance of the couch may be different from the moving distance reported by the position encoder. For example, the moving distance measured by the position encoder may be 0.1 mm, and the actual moving distance may be 0.12 mm. In some embodiments, the processing device 140 may determine whether the moving distance of the couch measured by the position encoders is correct by comparing with a distance between the first member and the second member (estimated based on their respective representations) in the at least one first image. The processing device 140 may determine whether the distance between the first member and the second member in the at least one first image is the same as a distance reported by the RT system 100. As used herein, two values (e.g., two distances, two positions) are considered the same if the difference between the two values is below a threshold. As used herein, two values (e.g., two distances) are considered different if the difference between the two values exceeds a threshold. In response to determining that the distance between the first member and the second member in the at least one first image is different from the distance reported by the RT system 100, the processing device 140 may determine that the moving distance of the couch reported by the position encoders is inaccurate, and the couch mechanism (e.g., a mechanical structure of the couch) may need to be calibrated.

In some embodiments, the processing device 140 may determine an image scale of a reconstructed image acquired by the first device or the second device based on the distance between the first member and the second member. The image scale may be presented in terms of, e.g., a pixel distance per one millimeter. In some embodiments, the processing device 140 may determine a pixel distance (or a voxel distance) between the first member and the second member in the image domain. The processing device 140 may determine the image scale based on the pixel distance between the first member and the second member in the image domain and the distance between the first member and the second member in the physical world. For example, the processing device 140 may determine the image scale by dividing the pixel distance between the first member and the second member in the image domain by the distance between the first member and the second member in the physical world.

In some embodiments, a treatment plan for a subject may include one or more planning isocenters. As used herein, a planning isocenter refers to a location of an isocenter (e.g., a geometric rotational isocenter) or a reference point (other than the geometric rotational isocenter) relative to a treatment region (or an imaging region) of the subject in a treatment plan. At least one planning isocenter of the one or more planning isocenters may be different from the first isocenter of the first device or the second isocenter of the second device. The phantom may be placed in the vicinity of a specific planning isocenter and imaged by the first device to generate at least one first image. A position of the planning isocenter may be determined based on the at least one first image as described in connection with operations 530 and 540. The phantom may then be imaged by the second device to generate at least one second image. The position of the phantom during the acquisition of the at least one first image may be the same as the position of the phantom during the acquisition of the at least one second image. That is, the couch may be stationary during the acquisition of the at least one first image and the acquisition of the at least one second image. The position of the planning isocenter in the at least one second image may be determined. In some embodiments, the position of the planning isocenter in the at least one second image may be determined by compensating for an offset of the phantom from the specific planning isocenter, compensating for an angular offset between the coupling member and the Z-axis, an angular offset between the cross member and the X-axis, and/or a distance between the first member and the second member. When the subject is treated by the first device, a treatment position of the subject, where a treatment isocenter identified from a treatment image (e.g., a CT acquired by the second device) aligns with the specific planning isocenter, may need to be determined. The treatment isocenter may refer to an isocenter (e.g., a central point) of a target (e.g., a tumor) of the subject. In some embodiments, the treatment position of the subject may be determined by compensating for the effects due to such as, e.g., a couch sag due to a weight of the subject and/or the weight of the couch 114.

Figure 6:
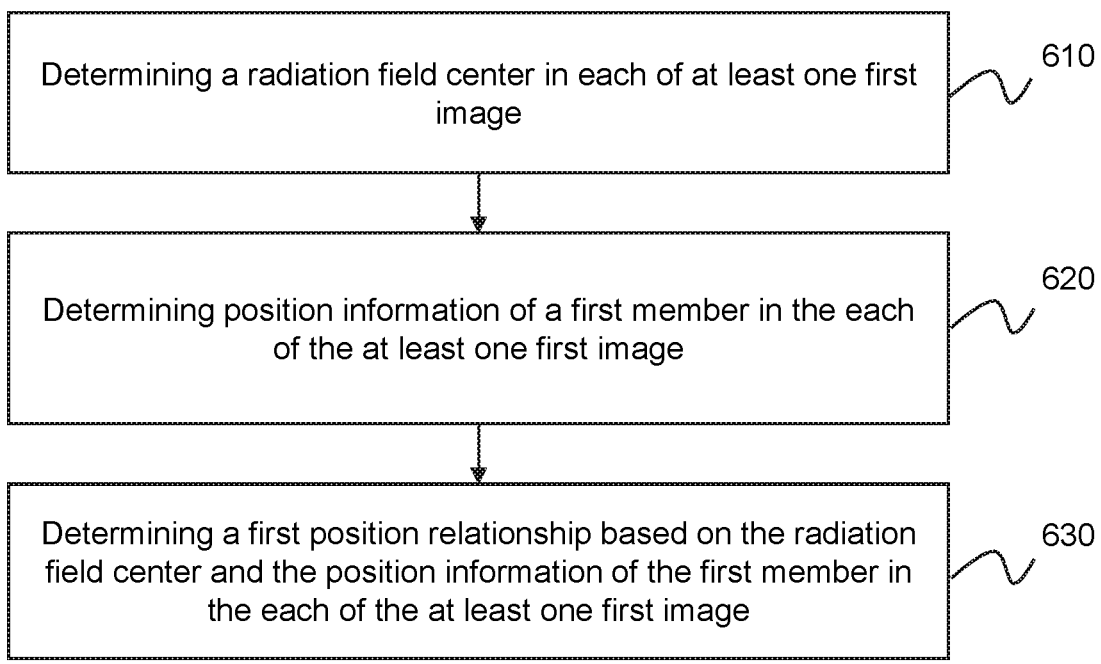
FIG. 6 is a flowchart illustrating an exemplary process for determining a position relationship between a first isocenter of a first device and a first member of a phantom according to some embodiments of the present disclosure.

FIG. 6 is a flowchart illustrating an exemplary process for determining a position relationship between a first isocenter of a first device and a first member of a phantom according to some embodiments of the present disclosure. In some embodiments, process 600 may be executed by the RT system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600.

In 610, the processing device 140 (e.g., the first determination module 420) may determine a radiation field center in each of at least one first image.

As used herein, a radiation field center in an image refers to a center point in the image. The radiation field center in a first image may correspond to a central axis of a radiation field associated with the first image. In some embodiments, the processing device 140 may identify the radiation field center in the each image, and determine image coordinates of the radiation field center in the first image in an image coordinate system. For example, the processing device 140 may identify radiation field edges in the first image based on one or more object detection algorithms (e.g., a Hough transform (HT)-based algorithm). The processing device 140 may then identify a center point that is closest to the radiation field edges in the first image. As used herein, a point closest to a plurality of lines (e.g., the plurality of radiation field edges) in the space indicates that a sum of a plurality of distances between the point and the plurality of lines is less than that of any other points in the space. The distance between a point and a line may refer to a shortest distance between the point and the line.

In 620, the processing device 140 (e.g., the first determination module 420) may determine position information of a first member in each of the at least one first image.

The position information of the first member in the first image may include a position of a reference point (e.g., a center point) of the first member in the first image. In some embodiments, the processing device 140 may identify a center point of the first member in the first image, and determine image coordinates of the center point of the first member in the first image in the image coordinate system. For example, the processing device 140 may identify, based on one or more object detection algorithms, a representation of the first member (or referred to as the first member in the image for brevity) in the first image. The processing device 140 may then identify a center point of the first member in the first image. For illustration purposes, if the first member is a sphere, the processing device 140 may determine a point at an equal distance from each point on the surface of the sphere as the center point of the sphere.

In 630, the processing device 140 (e.g., the first determination module 420) may determine a first position relationship between a first isocenter and the first member of the phantom based on the radiation field center and the position information of the first member in each of the at least one first image.

In some embodiments, the processing device 140 may determine a position of a first isocenter relative to the first member in a coordinate system (e.g., the coordinate system 160 as shown in FIG. 1) of the RT system 100 based on the image coordinates of the radiation field center in the each first image, the image coordinates of the first member in the each first image, and coordinates of the first member in the coordinate system 160. For example, the processing device 140 may determine a position of the central axis (or geometric centroid, or monitor-unit weighted geometric centroid) of the radiation field corresponding to the radiation field center in the each first image in the image coordinate system. The processing device 140 may further determine a point that is closer to the plurality of central axes than any other points in the space as the first isocenter. The processing device 140 may determine an average position of a plurality of center points (e.g., centroid) of the first member in the plurality of first images, and determine image coordinates of the average position. The processing device 140 may determine coordinates of the first isocenter in the coordinate system 160 based on image coordinates of the first isocenter and a transformation relationship between the image coordinate system and the coordinate system 160. The transformation relationship between the image coordinate system and the coordinate system 160 may be determined based on the coordinates of the center point of the first member in the coordinate system 160 and the image coordinates of the average position of the center points of the first member in the at least one first image in the image coordinate system. For illustration purposes, assuming that a transformation relationship between the image coordinate system and the coordinate system 160 is M, and the image coordinates of the first isocenter is (X, Y, Z), the processing device 140 may determine that the coordinates of the first isocenter in the coordinate system 160 is (X, Y, Z)*M.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. Additionally, the order of the process 600 may not be intended to be limiting.

In some embodiments, the processing device 140 may determine a first isocenter distribution based on the position of the first isocenter and a position of the radiation field center in the at least one first image. For example, the processing device 140 may determine a plurality of distances between the position of the first isocenter and a plurality of positions of the radiation field centers in the plurality of first images. The processing device 140 may select a specific distance (e.g., a mean distance, a median distance, a maximum distance, a minimum distance) from the plurality of distances as a radius of the first isocenter distribution.

Figure 7:
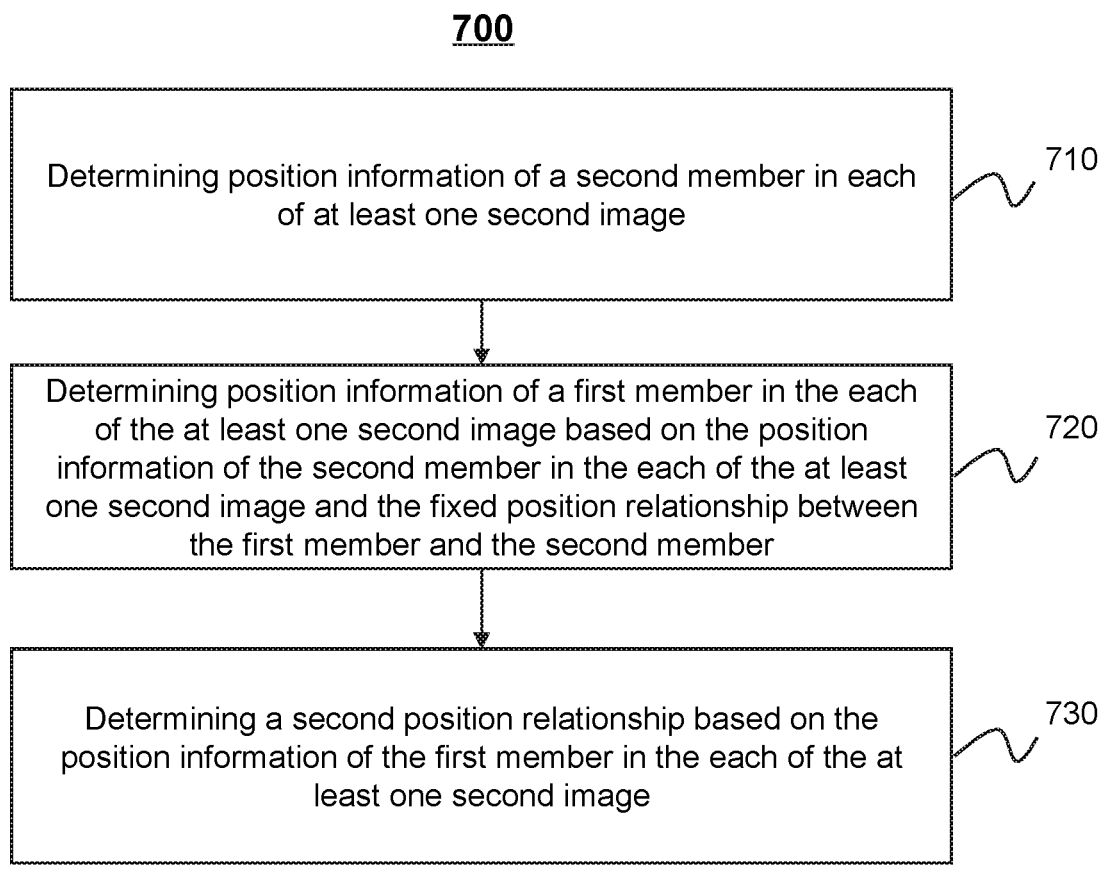
FIG. 7 is a flowchart illustrating an exemplary process for determining a position relationship between a second isocenter of a second device and a first member of a phantom according to some embodiments of the present disclosure.

FIG. 7 is a flowchart illustrating an exemplary process for determining a position relationship between a second isocenter of a second device and a first member of a phantom according to some embodiments of the present disclosure. In some embodiments, process 700 may be executed by the RT system 100. For example, the process 700 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700.

In 710, the processing device 140 (e.g., the second determination module 430) may determine position information of a second member in each of at least one second image.

In some embodiments, the processing device 140 may determine the position information of a second member and a coupling member in each of at least one second image. The position information of the second member and the coupling member in the second image may include a position of a reference point (e.g., a center point, e.g., centroid) of the second member in the image and an extending direction of the coupling member in the second image. In some embodiments, the processing device 140 may identify a center point of the second member and an extending direction of the coupling member in the image based on one or more object detection algorithms as described elsewhere in the present disclosure. For instance, the processing device 140 may identify, based on one or more object detection algorithms, a representation of the second member (or referred to as the second member in the image for brevity) and a representation of the coupling member in the second image (or referred to as the coupling member in the image for brevity). The processing device 140 may then identify a center point of the second member in the image and the extending direction of the coupling member accordingly.

In 720, the processing device 140 (e.g., the second determination module 430) may determine position information of a first member in the each of the at least one second image based on the position information of the second member in the each of the at least one second image and the fixed position relationship between the first member and the second member.

In some embodiments, the processing device 140 may determine the position information of the first member in the each second image based on the position of the second member, the extending direction of the coupling member, and a distance between the center point of the first member and the center point of the second member. For illustration purposes, if image coordinates of a center point of the second member in a second image is (X, Y, Z), a distance between a center point of the first member and the center point of the second member is A, and the extending direction of the coupling member is along a positive Z-direction of the image coordinate system, the processing device 140 may determine that image coordinates of the center of the first member is (X, Y, Z+A).

In 730, the processing device 140 (e.g., the second determination module 430) may determine a second position relationship between a second isocenter and the first member of the phantom based on the position information of the first member in the each of the at least one second image.

In some embodiments, the processing device 140 may identify an image center in the each of the at least one second image, and determine a position (e.g., image coordinates) of the image center in the each second image in the image coordinate system. The processing device 140 may determine an average position of the at least one image center in the at least one second image as the position of the second isocenter. The processing device 140 may determine an average position of the center point of the first member in the at least one second image, and determine image coordinates of the average position. For illustration purposes, assuming that first coordinates of the center point of the first member in a second image A is ($X_1$, second coordinates of the center point of the first member in a second image B is ($X_2$, $Y_2$, $Z_2$), third coordinates of the center point of the first member in a second image C is ($X_3$, $Y_3$, $Z_3$), and fourth coordinates of the center point of the first member in a second image D is ($X_4$, $Y_4$, $Z_4$), the processing device 140 may determine that coordinates of the average position is (($X_1+X_2+X_3+X_4$)/4, ($Y_1+Y_2+Y_3+Y_4$)/4, ($Z_1+Z_2+Z_3+Z_4$)/4). The processing device 140 may determine coordinates of the second isocenter in the coordinate system 160 based on image coordinates of the second isocenter and a transformation relationship between the image coordinate system and the coordinate system 160. The transformation relationship between the image coordinate system and the coordinate system 160 may be determined based on the coordinates of the center point of the first member in the coordinate system 160 and the image coordinates of the average position of the center point of the first member in the at least one second image in the image coordinate system. For illustration purposes, assuming that a transformation relationship between the image coordinate system and the coordinate system 160 is N, and the image coordinates of the second isocenter is (X, Y, Z), the processing device 140 may determine that the coordinates of the second isocenter in the coordinate system 160 is (X, Y, Z)*N.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above. Additionally, the order of the process 700 may not be intended to be limiting.

In some embodiments, the processing device 140 may determine a second isocenter distribution based on the position of the second isocenter and a position of the image center in the at least one second image. For example, the processing device 140 may determine a plurality of distances between the position of the second isocenter and a plurality of positions of the image centers in the plurality of second images. The processing device 140 may select a specific distance (e.g., a mean distance, a median distance, a maximum distance, a minimum distance) from the plurality of distances as a radius of the second isocenter distribution.

Figure 8:
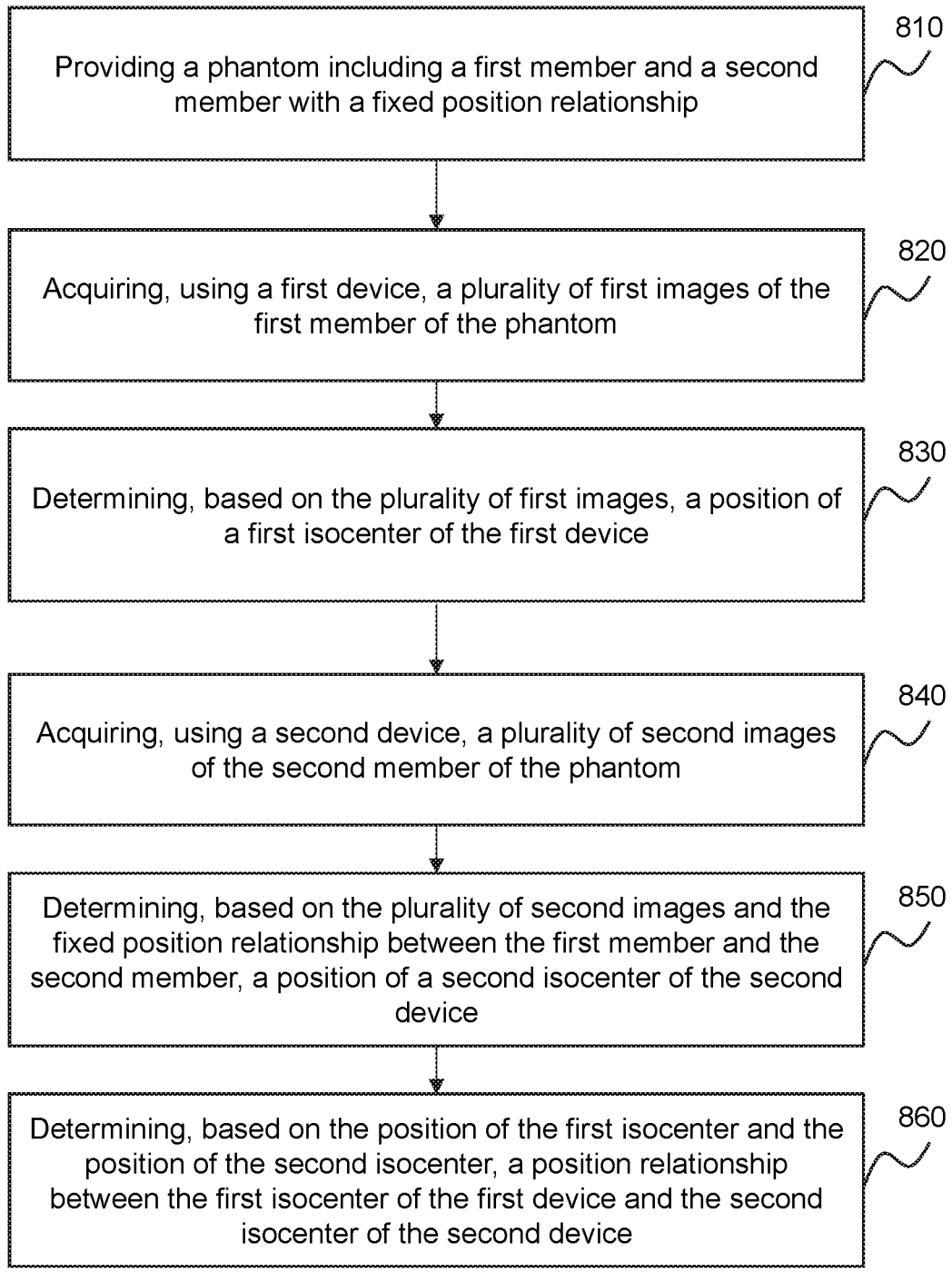
FIG. 8 is a flowchart illustrating an exemplary process for determining a position relationship between a first isocenter of a first device and a second isocenter of a second device according to some embodiments of the present disclosure.

FIG. 8 is a flowchart illustrating an exemplary process for determining a position relationship between a first isocenter of a first device and a second isocenter of a second device according to some embodiments of the present disclosure. In some embodiments, process 800 may be executed by the RT system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800.

In 810, a phantom including a first member and a second member with a fixed position relationship (e.g., connected by a coupling member) may be provided. More descriptions for the phantom may be found elsewhere in the present disclosure (e.g., operation 510 in FIG. 5, and the descriptions thereof).

In 820, the processing device 140 (e.g., the acquisition module 410) may acquire, using the first device (e.g., the first device 116), a plurality of first images of the first member of the phantom. More descriptions for acquiring the plurality of first images may be found elsewhere in the present disclosure (e.g., operation 520 in FIG. 5, and the descriptions thereof), which are not repeated here.

In 830, the processing device 140 (e.g., the first determination module 420) may determine, based on the plurality of first images, a position of a first isocenter of the first device.

In some embodiments, the processing device 140 may determine position information of the first member (e.g., image coordinates of a center point of the first member) in each first image of the plurality of first images in an image coordinate system. The processing device 140 may determine the position of the first isocenter based on the position information of the first member in the each first image of the plurality of first images in the image coordinate system. For example, the processing device 140 may determine an average position of a plurality of center points of the first member in the plurality of first images as a position of the first isocenter. For illustration purposes, assuming that first coordinates of the center point of the first member in a first image A is $(X_1, Y_1, Z_1)$, second coordinates of the center point of the first member in a first image B is $(X_2, Y_2, Z_2)$, third coordinates of the center point of the first member in a first image C is $(X_3, Y_3, Z_3)$, and fourth coordinates of the center point of the first member in a first image D is $(X_4, Y_4, Z_4)$, the processing device 140 may determine that coordinates of the first isocenter is $((X_1+X_2+X_3+X_4)/4, (Y_1+Y_2+Y_3+Y_4)/4, (Z_1+Z_2+Z_3+Z_4)/4)$. The processing device 140 may determine coordinates of the first isocenter in the coordinate system 160 based on the image coordinates of the average position and a transformation relationship between the image coordinate system and the coordinate system 160.

In some embodiments, the processing device 140 may determine a first isocenter distribution based on the position of the first isocenter and the plurality of positions of the center points of the first member in the image coordinate system. For example, the processing device 140 may determine a plurality of distances between the position of the first isocenter and the plurality of positions of the center points of the first member in the image coordinate system. The processing device 140 may select a specific distance (e.g., a mean distance, a median distance, a maximum distance, a minimum distance) from the plurality of distances as a radius of the first isocenter distribution.

In 840, the processing device 140 (e.g., the acquisition module 410) may acquire, using a second device, a plurality of second images of the second member of the phantom. In some embodiments, the processing device 140 may acquire a plurality of second images of the second member and the coupling member of the phantom. More descriptions for acquiring the plurality of second images may be found elsewhere in the present disclosure (e.g., operation 540 in FIG. 5, and the descriptions thereof), which are not repeated here.

In 850, the processing device 140 (e.g., the second determination module 430) may determine, based on the plurality of second images and the fixed position relationship between the first member and the second member, a position of a second isocenter of the second device.

In some embodiments, the processing device 140 may determine position information of the second member in each second image of the plurality of second images in the image coordinate system. The processing device 140 may determine position information of the first member in the each second image of the plurality of second images based on the position information of the second member in the each second image of the plurality of second images in the image coordinate system and the fixed position relationship between the first member and the second member. The processing device 140 may determine the position of the second isocenter based on the position information of the first member in the each second image of the plurality of second images in the image coordinate system. For example, for the each second image of the plurality of first images, the processing device 140 may determine a position of the first member (e.g., image coordinates of the center point of the first member) in the second image in the image coordinate system based on position information of the second member and the coupling member in the second image. The processing device 140 may determine an average position of a plurality of center points of the first member in the plurality of second images as a position of the second isocenter. The processing device 140 may determine coordinates of the second isocenter in the coordinate system 160 based on the image coordinates of the average position and a transformation relationship between the image coordinate system and the coordinate system 160.

In some embodiments, the processing device 140 may determine a second isocenter distribution based on the position of the second isocenter and the plurality of positions of the center points of the first member in the image coordinate system. For example, the processing device 140 may determine a plurality of distances between the position of the second isocenter and the plurality of positions of the center points of the first member in the image coordinate system. The processing device 140 may select a specific distance (e.g., a mean distance, a median distance, a maximum distance, a minimum distance) from the plurality of distances as a radius of the second isocenter distribution.

In 860, the processing device 140 (e.g., third determination module 440) may determine, based on the position of the first isocenter and the position of the second isocenter, a position relationship between the first isocenter of the first device and the second isocenter of the second device.

In some embodiments, the processing device 140 may determine a distance between the first isocenter and the second isocenter based on the position of the first isocenter and the position of the second isocenter. In some embodiments, the processing device 140 may determine whether the distance between the first isocenter and the second isocenter satisfies a first preset condition as described elsewhere in the present disclosure (e.g., FIG. 5 and the descriptions thereof), which are not repeated here. In some embodiments, the processing device 140 may determine whether the first isocenter distribution and/or the second isocenter distribution satisfies a second preset condition. For example, the processing device 140 may determine whether the radius of the first isocenter distribution (or the radius of the second isocenter distribution) satisfies the second preset condition (e.g., less than a radius threshold). In response to determining that the radius of the first isocenter distribution (or the radius of the second isocenter distribution) does not satisfy the preset condition, the processing device 140 may adjust one of the first device or the second device, as described elsewhere in the present disclosure. See, e.g., FIG. 5 and relevant description thereof, which are not repeated here.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. Additionally, the order of the process 500 may not be intended to be limiting.

In some embodiments, an angular offset of an extending direction of the coupling member along the Z-axis direction, and an angular offset of an extending direction of the cross member along the X-axis direction in the coordinate system 160 may be measured when the phantom is placed at a first position and/or a second position. One or more rotation components of the couch during the movement of the couch between the first position and the second position may be determined as described elsewhere in the present disclosure. The position of the first isocenter and/or the position of the second isocenter may be corrected to compensated for the angular offsets and the rotation components of the couch.

FIGS. 9A-9C are schematic diagrams illustrating exemplary phantoms according to some embodiments of the present disclosure.

As illustrated in FIG. 9A, a phantom 900A may include a first member A, a second member B, and a coupling member C. The first member A and the second member B may be spheres, and the coupling member may be a rod. The first member A and the second member B may be connected by the coupling member C. The coupling member C may have a first end a and a second end b. The first end a may be connected to an edge of the first member A, and the second end b may be connected to an edge of the second member B.

As illustrated in FIG. 9B, a phantom 900B may be similar to the phantom 900A, except for certain components or features. The phantom 900B may further include a cross member D disposed on a center point on the coupling member C between the first member A and the second member B, and perpendicular to the coupling member C.

As illustrated in FIG. 9C, a phantom 900C may be similar to the phantom 900B, except for certain components or features. The first end a of the coupling member may extend beyond the first member A, and the second end b may extend beyond the second member B. The longer the coupling member, the more precisely the angle between an extending direction of the coupling member and the Z-axis can be measured. However, if the coupling member is too long, it may be difficult to fabricate the phantom with a good precision. In addition, the transport, maneuverability, and/or storage of such a phantom may become more difficult.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for isocenter calibration implemented on a computing device having at least one processor and at least one storage device, the method comprising:
   providing a phantom including a first member and a second member with a fixed position relationship;
   acquiring, using a first device, at least one first image of the first member of the phantom;
   determining, based on the at least one first image, a first position relationship between a first isocenter of the first device and the first member;
   acquiring, using a second device, at least one second image of the second member of the phantom;
   determining, based on the at least one second image and the fixed position relationship between the first member and the second member, a second position relationship between a second isocenter of the second device and the first member; and
   determining, based on the first position relationship and the second position relationship, a third position relationship between the first isocenter of the first device and the second isocenter of the second device.

2. The method of claim 1, wherein determining, based on the at least one first image, a first position relationship between a first isocenter of the first device and the first member comprises:
   determining a radiation field center in each of the at least one first image;
   determining position information of the first member in the each of the at least one first image; and
   determining the first position relationship based on the radiation field center and the position information of the first member in the each of the at least one first image.

3. The method of claim 1, wherein determining, based on the at least one second image and the fixed position relationship between the first member and the second member, a second position relationship between a second isocenter of the second device and the first member comprises:
   determining position information of the second member in each of the at least one second image;
   determining position information of the first member in the each of the at least one second image based on the position information of the second member in the each of the at least one second image and the fixed position relationship between the first member and the second member; and
   determining the second position relationship based on the position information of the first member in the each of the at least one second image.

4. The method of claim 1, further comprising:
   placing the phantom at a first position with respect to the first device before the acquisition of the at least one first image; and
   causing a couch to move the phantom from the first position to a second position with respect to the second device after the acquisition of the at least one first image and before the acquisition of the at least one second image.

5. The method of claim 4, further comprising:
   determining one or more translation and rotation components of the couch during the movement of the couch.

6. The method of claim 1, further comprising:
   determining whether the third position relationship satisfies a preset condition; and
   adjusting one of the first device or the second device in response to determining that the third position relationship does not satisfy the preset condition.

7. The method of claim 1, wherein
   the first device includes a megavoltage (MV) treatment source, and
   the second device includes a kilovoltage (kV) imaging source.

8. The method of claim 7, wherein a first radius of the first member is larger than a second radius of the second member.

9. The method of claim 7, wherein
the first member is made of a first material,
the second member is made of a second material, and
an atomic number of the first material is higher than an atomic number of the second material.

10. The method of claim 9, wherein
the first material includes a metal, and
the second material includes plastic.

11. The method of claim 1, wherein the first member and the second member are connected by a coupling member.

12. The method of claim 11, wherein
the coupling member has a first end corresponding to the first member and a second end corresponding to the second member, and
at least one end of the first end or the second end of the coupling member extends beyond a corresponding member of the phantom.

13. The method of claim 11, wherein the phantom includes a second coupling member disposed at an angle with the coupling member.

14. The method of claim 1, wherein the first device includes a positron emission tomography (PET) device or a single photon emission computed tomography (SPECT) device, and the second device includes a CT device.

15. The method of claim 14, wherein a PET and/or SPECT imageable isotope is present in the phantom.

16. A method for isocenter calibration implemented on a computing device having at least one processor and at least one storage device, the method comprising:
providing a phantom including a first member and a second member with a fixed position relationship,
acquiring, using a first device, a plurality of first images of the first member of the phantom;
determining, based on the plurality of first images, a position of a first isocenter of the first device;
acquiring, using a second device, a plurality of second images of the second member of the phantom;
determining, based on the plurality of second images and the fixed position relationship between the first member and the second member, a position of a second isocenter of the second device; and
determining, based on the position of the first isocenter and the position of the second isocenter, a position relationship between the first isocenter of the first device and the second isocenter of the second device.

17. The method of claim 16, wherein determining, based on the plurality of first images, a position of a first isocenter of the first device comprises:
determining position information of the first member in each of the plurality of first images; and
determining the position of the first isocenter based on the position information of the first member in the each of the plurality of first images.

18. The method of claim 16, wherein determining, based on the plurality of second images and the fixed position relationship between the first member and the second member, a position of a second isocenter of the second device comprises:
determining position information of the second member in each of the plurality of second images;
determining position information of the first member in the each of the plurality of second images based on the position information of the second member in the each of the plurality of second images and the fixed position relationship between the first member and the second member; and
determining the position of the second isocenter based on the position information of the first member in the each of the plurality of second images.

19. The method of claim 16, further comprising:
determining a first isocenter distribution based on the plurality of first images; and
determining a second isocenter distribution based on the plurality of second images.

20. A system for isocenter calibration, comprising:
at least one storage device storing a set of instructions; and
at least one processor in communication with the at least one storage device, when executing the stored set of instructions, the at least one processor causes the system to perform operations including:
providing a phantom including a first ember and a second member with a fixed position relationship;
acquiring, using a first device, at east one first image of the first member of the phantom;
determining, based on the at least one first image, a first position relationship between a first isocenter of the first device and the first member;
acquiring, using a second device, at least one second image of the second member of the phantom;
determining, based on the at least one second image and the fixed position relationship between the first member and the second member, a second position relationship between a second isocenter of the second device and the first member; and
determining, based on the first position relationship and the second position relationship, a third position relationship between the first isocenter of the first device and the second isocenter of the second device.

* * * * *